(12) United States Patent (10) Patent No.: US 7,291,618 B2
Hulin et al. (45) Date of Patent: Nov. 6, 2007

(54) THERAPEUTIC COMPOUNDS

(75) Inventors: Bernard Hulin, Essex, CT (US); David W. Piotrowski, Groton, CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 11/129,277

(22) Filed: May 12, 2005

(65) Prior Publication Data

US 2005/0256310 A1 Nov. 17, 2005

Related U.S. Application Data

(60) Provisional application No. 60/664,305, filed on Mar. 21, 2005, provisional application No. 60/570,300, filed on May 12, 2004.

(51) Int. Cl.
*A61K 31/497* (2006.01)
*C07D 403/14* (2006.01)

(52) U.S. Cl. .................................. 514/252.19; 544/295

(58) Field of Classification Search ................. 544/295; 514/252.19
See application file for complete search history.

(56) References Cited

U.S. PATENT DOCUMENTS

| | | | |
|---|---|---|---|
| 2003/0078317 A1 | 4/2003 | Lin et al. | |
| 2003/0121450 A1 | 7/2003 | Lin et al. | |
| 2003/0167093 A1 | 9/2003 | Xu et al. | |
| 2003/0216777 A1 | 11/2003 | Tien et al. | |
| 2004/0003757 A1 | 1/2004 | Chern Lin et al. | |
| 2004/0022825 A1 | 2/2004 | Lagow | |
| 2004/0031420 A1 | 2/2004 | Lin et al. | |
| 2004/0076685 A1 | 4/2004 | Tas | |
| 2004/0137032 A1 | 7/2004 | Wang | |
| 2004/0175320 A1 | 9/2004 | Lin et al. | |
| 2004/0180091 A1 | 9/2004 | Lin | |
| 2004/0185181 A1 | 9/2004 | Matsumoto | |
| 2004/0186481 A1 | 9/2004 | Chern Lin et al. | |
| 2005/0069479 A1 | 3/2005 | Lin et al. | |
| 2005/0076813 A1 | 4/2005 | Lin et al. | |
| 2005/0101964 A1 | 5/2005 | Lin et al. | |

FOREIGN PATENT DOCUMENTS

| | | |
|---|---|---|
| CA | 2428271 | 5/2002 |
| EP | 1308439 | 5/2003 |
| EP | 1426366 | 6/2004 |
| EP | 1535906 | 6/2005 |
| JP | 06-228011 | 8/1994 |
| JP | 04026820 | 1/2004 |
| JP | 2005-170792 | * 6/2005 |
| JP | 05139107 | 6/2005 |
| WO | WO9534538 | 12/1995 |
| WO | WO 02076450 | 10/2002 |
| WO | WO 03000250 | 1/2003 |
| WO | WO 03002531 | 1/2003 |
| WO | WO 03002553 | 1/2003 |
| WO | WO 03035057 | 5/2003 |
| WO | WO 03/055418 | 7/2003 |
| WO | WO 03057144 | 7/2003 |
| WO | WO 03057666 | 7/2003 |
| WO | WO 03095425 | 11/2003 |
| WO | WO 03101449 | 12/2003 |
| WO | WO 03101958 | 12/2003 |
| WO | WO 2004007446 | 1/2004 |
| WO | WO 2004043940 | 5/2004 |
| WO | WO 2004046106 | 6/2004 |
| WO | WO 2004050022 | 6/2004 |
| WO | WO 2004071454 | 8/2004 |
| WO | WO 2004092128 | 10/2004 |
| WO | WO 2004110436 | 12/2004 |
| WO | WO 2004112701 | 12/2004 |
| WO | WO 2005009956 | 2/2005 |

(Continued)

OTHER PUBLICATIONS

Vippagunta et al Advanced Drug Delivery Reviews, vol. 48, pp. 3-26 (2001).*
Caldwell, C.G., et al., "Fluoropyrrolidine amides as dipeptidyl peptidase IV inhibitors", *Bioorganic & Medicinal Chemistry Letters*, vol. 14, pp. 1265-1268 (2004).
Lu, I., et al., "Glutamic acid analogues as potent dipeptidyl peptidase IV and 8 inhibitors", *Bioorganic & Medicinal Chemistry Letters*, vol. 15, pp. 3271-3275 (2005).
Mastracchio, A., et al., "Heterocycle Fused Cyclohexylglycine Derivatives as Novel Dipeptidyl Peptidase-IV Inhibitors", *Heterocycles*, vol. 82, pp. 203-206 (2004).

(Continued)

*Primary Examiner*—Johann R. Richter
*Assistant Examiner*—Ebenezer Sackey
(74) *Attorney, Agent, or Firm*—Gregg C. Benson; Scott A. McNeil

(57) ABSTRACT

The invention provides compounds of formula (I),

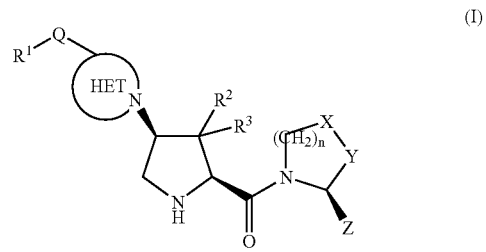

prodrugs and stereoisomers thereof, and the pharmaceutically acceptable salts of the compounds, prodrugs, and stereoisomers, wherein $R^1$, $R^2$, $R^3$, HET, n, Q, X, Y, and Z are as described herein; compositions thereof; and uses thereof in treating diabetic complications including diabetic neuropathy, diabetic nephropathy, diabetic microangiopathy, and the like.

4 Claims, No Drawings

FOREIGN PATENT DOCUMENTS

| WO | WO 2005023762 | 3/2005 |
|---|---|---|
| WO | WO 2005042533 | 5/2005 |
| WO | WO 2005044195 | 5/2005 |

OTHER PUBLICATIONS

Augustyns, KJL., et al., "Pyrrolidides: synthesis and structure-activity relationship as inhibitors of dipeptidyl peptidase IV", *Eur J Med Chem.*, vol. 32, pp. 301-309 (1997).

Sakashita, H., et al., "1-((S)-γ-Substituted prolyl)-(S)-2-cyanopyrrolidine as novel series of highly potent DPP-IV inhibitors", *Bioorganic & Medicinal Chemistry Letters*, vol. 15, pp. 2441-2445 (2005).

Xu, J., et al., "Discovery of potent and selective phenylalanine based dipeptidyl peptidase IV inhibitors", *Bioorganic & Medicinal Chemistry Letters*, vol. 15, pp. 2533-2536 (2005).

Fukushima, H., "Synthesis and structure-activity relationships of potent 3- or 4-substituted-2-cyanopyrrolodine dipeptidyl peptidase IV inhibitors", *Bioorganic & Medicinal Chemistry*, vol. 12, pp. 6053-6061 (2004).

* cited by examiner

THERAPEUTIC COMPOUNDS

CROSS-REFERENCE TO RELATED APPLICATION

This patent application claims the benefit of U.S. Provisional Application Ser. No. 60/664,305, filed on Mar. 21, 2005 and U.S. Provisional Application Ser. No. 60/570,300, filed on May 12, 2004, both of which are herein incorporated by reference in their entirety.

FIELD OF THE INVENTION

The invention relates to selective inhibitors of the enzyme dipeptidyl peptidase-IV (DPP-IV), pharmaceutical compositions thereof, and uses thereof for treating diseases and conditions associated with proteins that are subject to processing by DPP-IV.

BACKGROUND OF THE INVENTION

DPP-IV (EC 3.4.14.5) is a serine protease that preferentially hydrolyzes an N-terminal dipeptide from proteins having proline or alanine in the 2-position. DPP-IV is believed to be involved in diabetes, glucose tolerance, obesity, appetite regulation, lipidemia, osteoporosis, neuropeptide metabolism and T-cell activation, among others. Accordingly, administration of DPP-IV inhibitors in vivo prevents N-terminal degradation of substrate peptides, thereby resulting in higher circulating concentrations of such peptides, and therapeutic benefits associated with such elevated concentrations.

DPP-IV has been implicated in the control of glucose homeostasis because its substrates include the incretin peptides glucagon-like peptide 1 (GLP-1) and gastric inhibitory polypeptide (GIP). Cleavage of the N-terminal amino acids from these peptides renders them functionally inactive. GLP-1 has been shown to be an effective anti-diabetic therapy in Type 2 diabetic patients and to reduce the meal-related insulin requirement in Type 1 diabetic patients. GLP-1 and/or GIP are believed to regulate satiety, lipidemia and osteogenesis. Exogenous GLP-1 has been proposed as a treatment for patients suffering from acute coronary syndrome, angina and ischemic heart disease.

Administration of DPP-IV inhibitors in vivo prevents N-terminal degradation of GLP-1 and GIP, resulting in higher circulating concentrations of these peptides, increased insulin secretion and improved glucose tolerance. On the basis of these observations, DPP-IV inhibitors are regarded as agents for the treatment of Type 2 diabetes, a disease in which glucose tolerance is impaired. In addition, treatment with DPP-IV inhibitors prevents degradation of Neuropeptide Y (NPY), a peptide associated with a variety of central nervous system disorders, and Peptide YY which has been linked to gastrointestinal conditions such as ulcers, irritable bowel disease, and inflammatory bowel disease.

In spite of the early discovery of insulin and its subsequent widespread use in the treatment of diabetes, and the later discovery of and use of sulfonylureas (e.g. chlorpropamide, tolbutamide, acetohexamide, biguanides (e.g., phenformin), metformin, thiazolidinediones (e.g., rosiglitazone), and pioglitazone as oral hypoglycemic agents, the treatment of diabetes remains less than satisfactory.

The use of insulin, necessary in Type 1 diabetic patients and about 10% of Type 2 diabetic patients in whom currently available oral hypoglycemic agents are ineffective, requires multiple daily doses, usually by self-injection. Determination of the appropriate dosage of insulin necessitates frequent estimations of the glucose concentration in urine or blood. The administration of an excess dose of insulin causes hypoglycemia, with consequences ranging from mild abnormalities in blood glucose to coma, or even death.

Treatment of Type 2 diabetes usually comprises a combination of diet, exercise, oral agents, and in more severe cases, insulin. However, the clinically available hypoglycemics can have side effects that limit their use. A continuing need for hypoglycemic agents, which may have fewer side effects or succeed where others fail, is clearly evident.

Poorly controlled hyperglycemia is a direct cause of the multiplicity of complications (cataracts, neuropathy, nephropathy, retinopathy, cardiomyopathy) that characterize advanced Type 2 diabetes. In addition, Type 2 diabetes is a comorbid disease that frequently confounds hyperlipidemia, atherosclerosis and hypertension, adding significantly to the overall morbidity and mortality attributable to those diseases.

Epidemiological evidence has firmly established hyperlipidemia as a primary risk factor for cardiovascular disease (CVD) due to atherosclerosis. Atherosclerosis is recognized to be a leading cause of death in the United States and Western Europe. CVD is especially prevalent among diabetic subjects, at least in part because of the existence of multiple independent risk factors such as glucose intolerance, left ventricular hypertrophy and hypertension in this population. Successful treatment of hyperlipidemia in the general population, and in diabetic subjects in particular, is therefore of exceptional medical importance.

Hypertension (high blood pressure) is a condition that can occur in many patients in whom the causative agent or disorder is unknown. Such "essential" hypertension is often associated with disorders such as obesity, diabetes, and hypertriglyceridemia and it is known that hypertension is positively associated with heart failure, renal failure, and stroke. Hypertension can also contribute to the development of atherosclerosis and coronary disease. Hypertension, together with insulin resistance and hyperlipidemia, comprise the constellation of symptoms that characterize metabolic syndrome, also known as insulin resistance syndrome (IRS) and Syndrome X.

Obesity is a well-known and common risk factor for the development of atherosclerosis, hypertension, and diabetes. The incidence of obesity and its related sequelae is increasing worldwide. Currently, few pharmacological agents are available that reduce adiposity effectively and acceptably.

Osteoporosis is a progressive systemic disease characterized by low bone density and microarchitectural deterioration of bone tissue, with a consequent increase in bone fragility and susceptibility to fracture. Osteoporosis and the consequences of compromised bone strength are a significant cause of frailty, and of increased morbidity and mortality.

Heart disease is a major health problem throughout the world. Myocardial infarctions are a significant source of mortality among those individuals with heart disease. Acute coronary syndrome denotes patients who have or are at high risk of developing an acute myocardial infarction (MI).

Though there are therapies available for the treatment of diabetes, hyperglycemia, hyperlipidemia, hypertension, obesity, and osteoporosis there is a continuing need for alternative and improved therapies.

Various indications for DPP-IV inhibitors are discussed in Augustyns, et al., Curr. Medicinal Chem., 6, 311 (1999); Ohnuki, et al., Drugs of the Future, 1999, 24, 665-670 (1999); Villhauer, et al., Annual Reports in Medicinal Chemistry, 36, 191-200 (2001); Drucker, Expert Opin. Invest. Drugs, 12, 87-100 (2003); and Weideman, et al., Curr. Opin. Invest. Drugs, 4, 412-420 (2003).

Orally administered compounds that inhibit DPP-IV have recently been prepared, such as those disclosed in International Application WO 02/14271.

DPP-IV inhibitors, such as those disclosed in WO 02/14271, are believed to act by inhibiting the degradation of the natural hormones, GLP-1 and GIP. Therefore, it is important that a suitable concentration of the DPP-IV inhibitor be available in plasma to inhibit DPP-IV coincidently with the secretion of these GLP-1 and GIP hormones. To achieve such plasma concentrations, it is preferred that the DPP-IV inhibitor compounds maintain a higher plasma concentration over time than that which would be expected for other DPP-IV inhibitor compounds, such as those disclosed in WO 02/14271.

Therefore, what is needed is an orally administered DPP-IV inhibitor compound that has equivalent or better DPP-IV inhibitory activity and that maintains a higher plasma concentration over time.

SUMMARY OF THE INVENTION

The present invention relates to compounds having the structure of Formula (I)

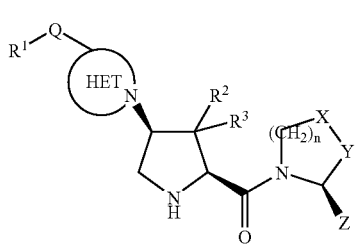

(I)

or a prodrug thereof, or a pharmaceutically acceptable salt of said compound or prodrug, or a solvate of said compound, prodrug or salt, wherein:

$R^1$ is —$(C_1-C_6)$alkyl, —$(C_1-C_6)$alkoxy, —$(C_1-C_6)$arylalkyl, —$NR^aR^b$, hydroxy, cyano, aryl, or heteroaryl, wherein said —$(C_1-C_6)$alkyl, said aryl, or said heteroaryl is optionally substituted independently with one to three —COOH, —C(O)$(C_1-C_6)$alkoxy, —C(O)$(C_1-C_6)$alkyl, —C(O)$NR^aR^b$, cyano, halogen, nitro, trifluoromethyl, —$(C_1-C_6)$alkyl, —$(C_1-C_6)$alkoxy, —$(C_3-C_6)$cycloalkyl, or phenyl, and wherein $R^a$ and $R^b$ are, independently, hydrogen, —$(C_1-C_6)$alkyl, aryl, or heteroaryl, or $R^a$ and $R^b$, taken together with the nitrogen atom to which they are attached, form a four- to six-membered heterocyclic ring, wherein said ring optionally incorporates an additional one or two nitrogen, oxygen, or sulfur ring heteroatoms;

$R^2$ and $R^3$ are, independently, hydrogen, halogen, —$(C_1-C_6)$alkyl, or —$(C_3-C_8)$cycloalkyl;

Q is a covalent bond, —C(O)—, or —$SO_2$—;

HET is a heterocycloalkyl ring moiety, optionally substituted with: (A) one to four —$(C_1-C_6)$alkyl, optionally substituted with one to six halogen atoms, —$(C_1-C_6)$alkoxy, cyano, halogen, hydroxy, or —$NR^aR^b$, or (B) —$(C_1-C_6)$arylalkyl, optionally substituted with one to six halogen atoms, —$(C_1-C_6)$alkoxy, cyano, halogen, hydroxy, or —$NR^aR^b$;

n is zero or one;

X is —$CH_2$—, —CHF—, or —$CF_2$— and Y is —$CH_2$—, —CHF—, or —$CF_2$—, provided that when n is one X and Y are not both $CH_2$ and when n is zero X is —$CH_2$—; and Z is hydrogen or cyano.

The present invention also relates to a pharmaceutical composition comprising a therapeutically effective amount of a compound of the present invention, or a prodrug thereof, or a pharmaceutically acceptable salt of the compound or prodrug, or a solvate of the compound, prodrug or salt, and a pharmaceutically acceptable carrier, vehicle, diluent or excipient.

The present invention further relates to a method of treating diabetes comprising administering to a mammal in need of such treatment a therapeutically effective amount of a compound of the present invention, or a prodrug thereof, or a pharmaceutically acceptable salt of the compound or of the prodrug, or a solvate of the compound, prodrug or salt. Preferably, the type of diabetes treated is Type 2 diabetes.

The present invention additionally relates to a method of treating a condition mediated by dipeptidyl peptidase-IV in a mammal comprising administering to said mammal in need of such treatment a therapeutically effective amount of a compound of the present invention, or a prodrug thereof, or a pharmaceutically acceptable salt of said compound or prodrug, or a solvate of said compound, prodrug or salt.

The compounds, and pharmaceutical compositions, of the present invention are useful for the treatment of diabetes, preferably Type 2 diabetes.

The compounds, and pharmaceutical compositions, of the present invention are also useful for the treatment of dipeptidyl peptidase-IV related conditions which include, but are not limited to, Type 2 diabetes; Type 1 diabetes, impaired glucose tolerance, hyperglycemia, metabolic syndrome (syndrome X and/or insulin resistance syndrome), glucosuria, metabolic acidosis, arthritis, cataracts, diabetic neuropathy, diabetic nephropathy, diabetic retinopathy, diabetic cardiomyopathy, obesity, conditions exacerbated by obesity, hypertension, hyperlipidemia, atherosclerosis, osteoporosis, osteopenia, frailty, bone loss, bone fracture, acute coronary syndrome, short stature due to growth hormone deficiency, infertility due to polycystic ovary syndrome, anxiety, depression, insomnia, chronic fatigue, epilepsy, eating disorders, chronic pain, alcohol addiction, diseases associated with intestinal motility, ulcers, irritable bowel syndrome, inflammatory bowel syndrome; short bowel syndrome; and the prevention of disease progression in Type 2 diabetes.

DETAILED DESCRIPTION

The terms used to describe the present invention have the following meanings herein.

The phrase "pharmaceutically acceptable" indicates that the designated carrier, vehicle, diluent, excipient(s), and/or salt is generally chemically and/or physically compatible with the other ingredients comprising the formulation, and physiologically compatible with the recipient thereof.

The carbon atom content of the various hydrocarbon-containing moieties herein may be indicated by a prefix designating the minimum and maximum number of carbon atoms in the moiety, for example, the prefixes $(C_a-C_b)$alkyl, and $C_{a-b}$alkyl, indicate an alkyl moiety of the integer "a" to "b" carbon atoms, inclusive. Thus, for example, $(C_1-C_6)$alkyl and $C_{1-6}$alkyl refer to an alkyl group of one to six carbon atoms inclusive.

The term "alkyl" denotes a straight or branched chain of carbon atoms, wherein the alkyl group optionally incorporates one or more double or triple bonds, or a combination of double bonds and triple bonds. Examples of alkyl groups include methyl, ethyl, propyl, isopropyl, butyl, isobutyl, vinyl, allyl, 2-methylpropenyl, 2-butenyl, 1,3-butadienyl, ethynyl, propargyl, and the like.

The term "alkoxy" refers to straight or branched, monovalent, saturated aliphatic chains of carbon atoms bonded to an oxygen atom that is attached to a core structure. Examples of alkoxy groups include methoxy, ethoxy, propoxy, butoxy, is obutoxy, tert-butoxy, and the like.

The term "cycloalkyl" denotes a saturated monocyclic or bicyclic cycloalkyl group. Cycloalkyl groups may be optionally fused to aromatic hydrocarbons such as benzene to form fused cycloalkyl groups, such as indanyl and the like. Examples of cycloalkyl groups include cyclopropyl, cyclobutyl, cyclopentyl, cyclohexyl, cycloheptyl, and the like.

The term "halogen" or "halo" represents chloro, bromo, fluoro, and iodo atoms and substituents.

The term "aryl" denotes a monocyclic or polycyclic aromatic hydrocarbon group, for example, anthracenyl, fluorenyl, naphthyl, phenanthrenyl, phenyl, and the like.

The term "arylalkyl" means an alkyl group, as defined hereinabove, wherein at least one of the hydrogen atoms thereof has been substituted with an aryl group, also as defined hereinabove. Examples of arylalkyl groups include, inter alia, benzyl groups.

The term "heterocycloalkyl", as employed with reference to HET hereinabove, refers to a saturated four- to eight-membered heterocyclic ring system, optionally fused to a five- or six-membered aromatic or heteroaromatic ring system. Examples of heterocycloalkyl groups comprise homopiperazinyl, piperazinyl, piperidyl, pyrrolidinyl, azetidinyl, 2-aza-bicyclo[2.2.1]heptanyl, 3-aza-bicyclo[3.1.0]hexanyl, 2,5-diaza-bicyclo[2.2.1]heptanyl, 5,6,7,8-tetrahydro-2H-imidazo[1,2-a]pyrazinyl, 5,6,7,8-tetrahydro[1,2,4]triazolo[4,3-a]pyrazinyl, 4,5,6,7-tetrahydropyrazolo[1,5-a]pyrazinyl, 5,6,7,8-tetrahydropyrido[3,4-d]pyrimidyl, 5,6,7,8-tetrahydropyrido[4,3-d]pyrimidyl, octahydropyrrolo[3,4-b]pyrrol, octahydropyrrolo[3,4-c]pyrrolyl, 6-azabicyclo[3.2.1]octanyl, 3,8-diazabicyclo[3.2.1]octanyl, 2,3-dihydrospiro[indene-1,4'-piperidyl], spiro[indene-1,4'-piperidyl], 1-oxa-8-azaspiro[4.5]decanyl, 8-azabicyclo[3.2.1]octanyl, 2,3,4,5-tetrahydrobenzo[f][1,4]oxazepinyl, hexahydro-2H-pyrrolo[3,4-d]isothiazolyl-1,1-dioxide, 2,7-diazaspiro[4.4]nonanyl, 6,7,8,9-tetrahydro-5H-[1,2,4]triazolo[4,3-g][1,4]diazepinyl, 5,6-dihydro-8H-imidazo[1,2-a]pyrazinyl, 5,6-dihydro-8H-[1,2,4]triazolo[4,3-a]pyrazinyl, 7,8-dihydro-5H-pyrido[4,3-a]pyrimidyl, 7,8-dihydro-5H-pyrido[4,3-d]pyrimidyl, pyrazolo[1,5-a]pyrimidyl, and the like.

The term "heteroaryl" denotes a monocyclic or polycyclic aromatic heterocyclic ring system. Examples of heteroaryl groups comprise benzoisothiazolyl, benzisoxazolyl, benzooxazolyl, benzothiazolyl, benzofuranyl, benzothienyl, benzimidazolyl, cinnolinyl, furanyl, furopyridyl, imidazolopyrimidyl, imidazolyl, indazolyl, indolyl, isoquinolyl, isothiazolyl, isoxadiazolyl, isoxazolyl, oxazolopyridyl, oxadiazolyl, oxazolyl, phthalazinyl, pteridinyl, pyrazinyl, pyridazinyl, pyrrolopyrimidyl, pyrrolopyridyl, pyrazolopyrimidyl, pyrazolyl, pyridyl, pyrimidyl, pyrrolyl, quinazolyl, quinolyl, quinoxalinyl, tetrazolyl, thiazolyl, thiadiazolyl, thiazolopyridyl, thienopyridyl, thienyl, triazinyl, triazolyl, 1,1-dioxo-1H-1,2-benzoisothiazolyl, oxazolopyridyl, and the like.

The term "oxo", means a carbonyl group formed by the combination of a carbon atom and an oxygen atom.

The term "substituted" means that a hydrogen atom on a molecule has been replaced with a different atom or molecule. The atom or molecule replacing the hydrogen atom is denoted as a "substituent."

The symbol "—" represents a covalent bond.

The phrase "inert solvent" refers to a solvent, or mixture of solvents, that does not interact with starting materials, reagents, intermediates, or products in a manner that adversely affects their desired properties.

The terms "treating", "treated", or "treatment" as employed herein includes preventative (e.g., prophylactic), palliative, and curative uses or results.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "mammal" is an individual animal that is a member of the taxonomic class Mammalia. The class Mammalia includes, for example, humans, monkeys, chimpanzees, gorillas, cattle, swine, horses, sheep, dogs, cats, mice and rats. In the present invention, the preferred mammal is a human.

Preferably, the compounds of the present invention have the structure of Formula (I) wherein:

$R^1$ is aryl or heteroaryl, optionally substituted independently with one to three cyano, halogen, nitro, trifluoromethyl, —($C_1$-$C_6$)alkyl, —($C_1$-$C_6$)alkoxy, —($C_3$-$C_6$)cycloalkyl, or phenyl;

$R^2$ is —H or —($C_1$-$C_6$)alkyl;

$R^3$ is —H —($C_1$-$C_6$)alkyl; and

HET is azetidinyl, piperazinyl, piperidinyl, pyrrolidinyl, 5,6-dihydro-8H-imidazo[1,2-a]pyrazin-7-yl, 5,6-dihydro-8H-[1,2,4]triazolo[4,3-a]pyrazin-7-yl, or 7,8-dihydro-5H-pyrido[4,3-a]pyrimidin-6yl.

More preferably, the compounds of the present invention have the structure of Formula (IA)

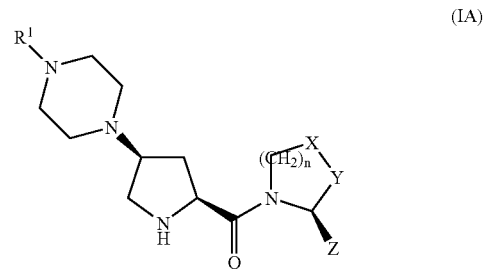

(IA)

wherein $R^1$ is benzoisothiazolyl, benzisoxazolyl, isothiazolyl, isoxazolyl, oxazolopyridyl, pyrazinyl, pyridinyl, pyrimidinyl, quinolinyl, quinoxalinyl, thiadiazolyl, triazinyl, or 1,1-dioxo-1H-1,2-benzoisothiazolyl.

In the present invention, it is preferred, for the compounds of Formula (IA), that $R^1$ is pyridinyl or pyrimidinyl and more preferred that $R^1$ is pyridinyl or pyrimidinyl, n is 1, X is —$CF_2$— and Y is —$CH_2$—.

In the present invention, the compound (3,3-difluoropyrrolidin-1-yl)-((2S,4S)-4-(4-(pyrimidin-2-yl)piperazin-1-yl)pyrrolidin-2-yl)methanone, or a prodrug thereof, or a pharmaceutically acceptable salt of said compound or said prodrug, is most preferred.

In an alternate embodiment, a compound selected from the group consisting of:

((2S,4S)-4-(3-(trifluoromethyl)-5,6-dihydro-[1,2,4]triazolo[4,3-a]pyrazin-7(8H)-yl)pyrrolidin-2yl)-(3,3-difluoropyrrolidin-1-yl)-methanone, (3,3-difluoropyrrolidin-1-yl)-((2S,4S)-4-(4-(oxazolo[5,4-b]pyridin-2-yl)piperazin-1-yl)pyrrolidin-2yl)-methanone, (3,3-difluoropyrrolidin-1-yl)-((2S,4S)-4-(4-(4-methylpyrimidin-2-yl)piperazin-1-yl)pyrrolidin-2-yl)-methanone, ((2S,4S)-4-(2-(trifluoromethyl)-7,8-dihydropyrido[4,3-d]pyrimidin-6(5H)-yl)pyrrolidin-2-yl)-(3,3-difluoropyrrolidin-1-yl)-methanone, ((S)-3-fluoro-pyrrolidin-1-yl)-{(2S,4S)-4-[4-(3-trifluoromethyl-pyridin-2-yl)-piperazin-1-yl]-pyrrolidin-2-yl}-methanone, ((S)-3-fluoro-pyrrolidin-1-yl)-[(2S,4S)-4-(2-trifluoromethyl-7,8-dihydro-5H-pyrido[4,3-d]pyrimidin-6-yl)-pyrrolidin-2-yl]-methanone, (3,3-difluoro-pyrrolidin-1-yl)-[(2S,4S)-4-(4-oxazolo[4,5-c]pyridin-2-yl-piperazin-1-yl)-pyrrolidin-2-yl]-methanone,

[(2S,4S)-4-(2-cyclopropyl-7,8-dihydro-5H-pyrido[4,3-d]pyrimidin-6-yl)-pyrrolidin-2-yl]-(3-fluoro-azetidin-1-yl)-methanone, (3,3-difluoro-pyrrolidin-1-yl)-[(2S,4S)-4-(2-ethoxy-7,8-dihydro-5H-pyrido[4,3-d]pyrimidin-6-yl)-pyrrolidin-2-yl]-methanone, 2-{4-[(3S,5S)-5-(3-fluoro-azetidine-1-carbonyl)-pyrrolidin-3-yl]-piperazin-1-yl}-nicotinonitrile, ((S)-3-fluoro-pyrrolidin-1-yl)-[(2S,4S)-4-(4-oxazolo[5,4-b]pyridin-2-yl-piperazin-1-yl)-pyrrolidin-2-yl]-methanone, (3-fluoro-azetidin-1-yl)-[(2S,4S)-4-(2-trifluoromethyl-7,8-dihydro-5H-pyrido[4,3-d]pyrimidin-6-yl)-pyrrolidin-2-yl]-methanone, 2-{4-[(3S,5S)-5-((S)-3-fluoro-pyrrolidine-1-carbonyl)-pyrrolidin-3-yl]-piperazin-1-yl}-nicotinonitrile, (3-fluoro-azetidin-1-yl)-{(2S,4S)-4-[4-(2-trifluoromethyl-quinolin-4-yl)-piperazin-1-yl]-pyrrolidin-2-yl}-methanone, ((3R*,4S*)-3,4-difluoro-pyrrolidin-1-yl)-[(2S,4S)-4-(2-trifluoromethyl-7,8-dihydro-5H-pyrido[4,3-d]pyrimidin-6-yl)-pyrrolidin-2-yl]-methanone, and ((3R*,4S*)-3,4-difluoro-pyrrolidin-1-yl)-[(2S,4S)-4-(4-oxazolo[5,4-b]pyridin-2-yl-piperazin-1-yl)-pyrrolidin-2-yl]-methanone, or a prodrug thereof, or a pharmaceutically acceptable salt of said compound or said prodrug, is preferred.

The compounds of the present invention contain all contain at least two stereogenic centers, specifically the (2S, 4S) pyrrolidin-2-yl, stereogenic centers shown below in Formula (I).

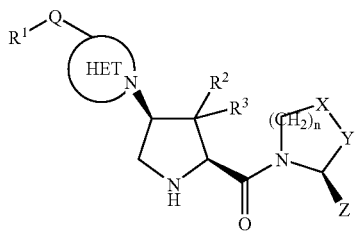

(I)

The compounds of the present invention may be resolved into the pure enantiomers by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired stereoisomer is converted into another chemical entity by one of the separation procedures described above, a further step is required to liberate the desired enantiomeric form. Alternatively, the specific stereoisomers may be synthesized by using an optically active starting material, by asymmetric synthesis using optically active reagents, substrates, catalysts or solvents, or by converting one stereoisomer into the other by asymmetric transformation.

Wherein said compounds contain one or more additional stereogenic centers, those skilled in the art will appreciate that all diastereoisomers and diastereoisomeric mixtures of the compounds illustrated and discussed herein are within the scope of the present invention. These diastereoisomers may be isolated by methods known to those skilled in the art, for example, by crystallization, gas-liquid or liquid chromatography. Alternatively, intermediates in the course of the synthesis may exist as racemic mixtures and be subjected to resolution by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired stereoisomer is converted into another chemical entity by one of the separation procedures described above, a further step is required to liberate the desired enantiomeric form. Alternatively, specific stereoisomers may be synthesized by asymmetric synthesis using optically active reagents, substrates, catalysts or solvents, or by converting one stereoisomer into the other by asymmetric transformation.

Certain compounds of Formula (I) may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of Formula (I) and mixtures thereof.

Practitioners will appreciate that certain compounds of Formula (I) may exist in tautomeric form, i.e., that an equilibrium exists between two isomers which are in rapid equilibrium with each other. A common example of tautomerism is keto-enol tautomerism, i.e.,

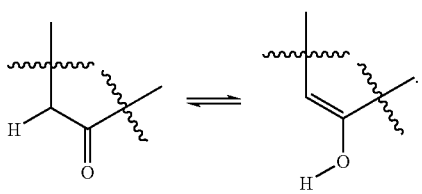

Examples of such compounds of the present invention include, inter alia, hydroxypyridines (pyridones) and hydroxypyrmidines (pyrimidones). In particular, a person skilled in the art will recognize that a hydroxypyridine of the instant invention can exist as two separate tautomers, e.g.,

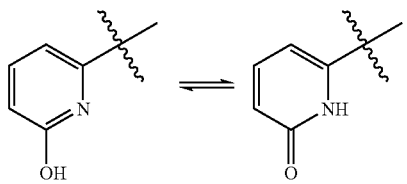

The degree to which one tautomer is present over the other depends upon various factors, including substitution pattern and solvent type. Other examples in accordance with the present invention will be recognized by those skilled in the art. All tautomeric forms of Formula (I) are included within the scope of the claimed invention.

The compounds of the present invention may exist in unsolvated as well as solvated forms with pharmaceutically acceptable solvents such as water, ethanol, and the like, and it is intended that the invention embrace unsolvated forms, solvated forms and mixtures of solvated forms.

Certain compounds of Formula (I) and their salts and solvates may exist in more than one crystal form. Polymorphs of compounds represented by Formula (I) form part of this invention and may be prepared by crystallization of a compound of Formula (I) under different conditions. For example, using different solvents or different solvent mixtures for recrystallization; crystallization at different temperatures; various modes of cooling, ranging from very fast to very slow cooling during crystallization. Polymorphs may also be obtained by heating or melting a compound of Formula (I) followed by gradual or fast cooling. The presence of polymorphs may be determined by solid probe nmr spectroscopy, ir spectroscopy, differential scanning calorimetry, powder X-ray diffraction or such other techniques.

This invention also includes isotopically-labeled compounds, which are identical to those described by Formula (I), but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, sulfur and fluorine, such as $^2H$, $^3H$, $^{13}C$, $^{14}C$, $^{15}N$, $^{18}O$, $^{17}O$, $^{35}S$, $^{36}Cl$, $^{125}I$, $^{129}I$, and $^{18}F$, respectively. Compounds of the present invention, prodrugs thereof, and pharmaceutically acceptable salts of the compounds or of the prodrugs which contain the aforementioned isotopes and/or other isotopes of other atoms are within the scope of this invention. Certain isotopically-labeled compounds of the present invention, for example those into which radioactive isotopes such as $^3H$ and $^{14}C$ are incorporated, are useful in drug and/or substrate tissue distribution assays. Tritiated (i.e., $^3H$), and carbon-14 (i.e., $^{14}C$), isotopes are particularly preferred for their ease of preparation and detectability. Further, substitution with heavier isotopes such as deuterium (i.e., $^2H$), can afford certain therapeutic advantages resulting from greater metabolic stability, for example increased in vivo half-life or reduced dosage requirements and, hence, may be preferred in some circumstances. Isotopically labeled compounds of Formula (I) of this invention and prodrugs thereof can generally be prepared by carrying out the procedures disclosed in the schemes and/or in the Examples below, by substituting a readily available isotopically labeled reagent for a non-isotopically labeled reagent.

Pharmaceutically acceptable salts, as used herein in relation to compounds of the present invention, include pharmaceutically acceptable inorganic and organic salts of said compound. These salts can be prepared in situ during the final isolation and purification of a compound, or by separately reacting the compound or prodrug with a suitable organic or inorganic acid and isolating the salt thus formed. Representative salts include, but are not limited to, the hydrobromide, hydrochloride, hydroiodide, sulfate, bisulfate, nitrate, acetate, trifluoroacetate, oxalate, besylate, palmitate, pamoate, malonate, stearate, laurate, malate, borate, benzoate, lactate, phosphate, hexafluorophosphate, benzene sulfonate, tosylate, formate, citrate, maleate, fumarate, succinate, tartrate, naphthylate, mesylate, glucoheptonate, lactobionate and laurylsulphonate salts, and the like. These may also include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. For additional examples see, for example, Berge, et al., J. Pharm. Sci., 66, 1-19 (1977).

The compounds of the present invention may be isolated and used per se or in the form of their pharmaceutically acceptable salts or solvates. In accordance with the present invention, compounds with multiple basic nitrogen atoms can form salts with varying number of equivalents of acid. It will be understood by practitioners that all such salts are within the scope of the present invention.

A prodrug of a compound of Formula (I) may be one formed in a conventional manner with a functional group of the compound, such as with an amino, hydroxy or carboxy group. The term "prodrug" means a compound that is transformed in vivo to yield a compound of Formula (I) or a pharmaceutically acceptable salt or solvate of the compound. The transformation may occur by various mechanisms, such as through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of the present invention incorporates an amine functional group, a prodrug can be formed by the replacement of a hydrogen atom in the amine group with a group such as R-carbonyl, RO-carbonyl, NRR'-carbonyl where R and R' are each independently $(C_1-C_{10})$ alkyl, $(C_3-C_7)$cycloalkyl, benzyl, or R-carbonyl is a natural α-aminoacyl or natural α-aminoacyl-natural α-aminoacyl, —C(OH)C(O)OY' wherein Y' is H, $(C_1-C_6)$alkyl or benzyl, —C(OY$_0$)Y$_1$ wherein Y$_0$ is $(C_1-C_4)$ alkyl and Y$_1$ is $(C_1-C_6)$ alkyl, carboxy($C_1$-$C_6$)alkyl, amino($C_1$-$C_4$)alkyl or mono-N— or di-N,N—($C_1$-$C_6$)alkylaminoalkyl, —C($Y_2$)$Y_3$ wherein $Y_2$ is H or methyl and $Y_3$ is mono-N— or di-N,N—($C_1$-$C_6$)alkylamino, morpholino, piperidin-1-yl or pyrrolidin-1-yl.

Similarly, if a compound of the present invention contains an alcohol functional group, a prodrug can be formed by the replacement of the hydrogen atom of the alcohol group with a group such as ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino($C_1$-$C_4$)alkanoyl, arylacyl and α-aminoacyl, or α-aminoacyl-α-aminoacyl, where each α-aminoacyl group is independently selected from the naturally occurring L-amino acids, P(O)(OH)$_2$, —P(O)(O($C_1$-$C_6$)alkyl)$_2$ or glycosyl (the radical resulting from the removal of a hydroxyl group of the hemiacetal form of a carbohydrate).

If a compound of the present invention contains a carboxylic acid functional group, a prodrug can comprise an ester formed by the replacement of the hydrogen atom of the acid group with a group such as ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$)alkyl.

In general, the compounds of Formula (I) of this invention may be prepared by methods that include processes known in the chemical arts, particularly in light of the description contained herein. Certain processes for the manufacture of the compounds of Formula (I) of this invention are illustrated by the following reaction schemes. Other processes are described in the experimental section. The methods disclosed in the instant Schemes and Examples are are intended for purposes of exemplifying the instant invention, and are not to be construed in any manner as limitations thereon.

Some of the starting compounds for the reactions described in the schemes and Examples are prepared as illustrated herein. All other starting compounds may be obtained from general commercial sources, such as Sigma-Aldrich Corporation, St. Louis, Mo.

In the discussions below, the following abbreviations are used: BOC (tert-butoxycarbonyl), Cbz (benzyloxycarbonyl), DMF (N,N-dimethylformamide), NMP (N-methyl-2-pyrrolidinone), DMAC (N,N-dimethylacetamide), DME (dimethoxyethane), DMSO (dimethylsulfoxide), EtOAC (ethyl acetate), EtOH (ethanol), MeOH (methanol), TFA (trifluoroacetic acid), TFAA (trifluoroacetic anhydride), TEA (triethylamine), THF (tetrahydrofuran), DIPEA (diisopropylethylamine), EDC (1-(3-dimethylaminopropyl)-3-carbodiimide)), DCC (dicyclohexylcarbodiimide), CDI (1,1'-carbonyldiimidazole), HATU (O-(7-azabenzotriazol-1-yl)-N,N,N',N'-tetramethyluronium hexafluorophosphate), HOAT (1-hydroxy-7-azabenzotriazole), HOBT (N-hydroxybenzotriazole), and EEDO (2-ethoxy-1-ethoxycarbonyl-1,2-dihydroquinoline).

A generalized method for preparing the compounds of formula (I) is depicted in Scheme 1 hereinbelow.

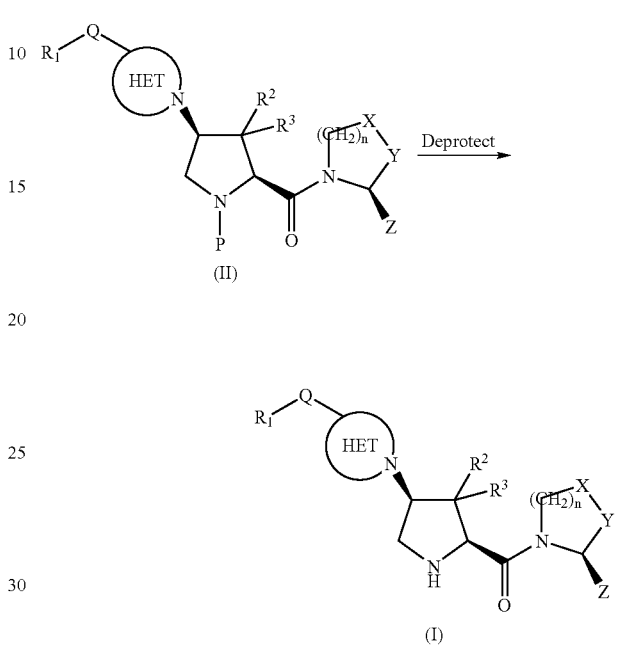

In Scheme 1, a compound of formula (II), prepared as described in Scheme 2, wherein P represents a nitrogen-protecting group, is deprotected according to known methods. If P represents BOC, deprotection is typically effected by first treating (II), dissolved in a solvent such as EtOAc, ether dioxane or water, with optional cooling at a suitable temperature, such as about 0° C., with acid (e.g., hydrogen chloride) for a suitable time, such as about 5 minutes to about an hour. The solution is allowed to warm to room temperature (RT), followed by stirring for an additional amount of time, typically an additional 30 minutes to about 16 hours. Preferably, the reaction mixture is stirred about 15 minutes, allowed to reach room temperature, then stirred an additional 30 minutes. Alternatively, (II) is dissolved in TFA and, after a suitable time (e.g., about 30 min to about 24 hours), excess TFA is removed in vacuo, and the residual product is triturated with a solvent such as ether. If P represents Cbz, deprotection may be performed by hydrogenolysis in the presence of catalyst, such as 10% palladium or palladium hydroxide, in a suitable solvent such as EtOH or EtOAC at a pressure of about 30 psi to about 60 psi, for a sufficient period of time, usually overnight, at a temperature of between about 20° C. and about 80° C. Preferably, hydrogenolysis is effected at a pressure of about 45 psi at room temperature.

The compounds of formula (II) may be prepared by coupling an appropriately-substituted carboxylic acid derivative (III) with an appropriately-substituted amine derivative (IV) as depicted hereinbelow in Scheme 2.

Scheme 2

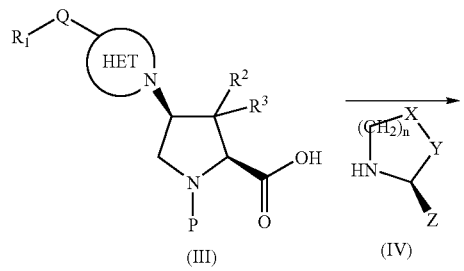
(III)      (IV)

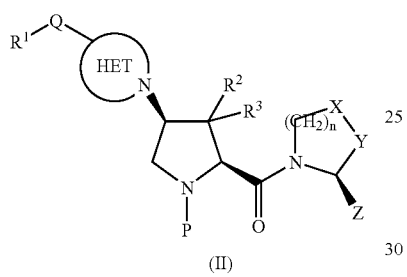
(II)

Scheme 3

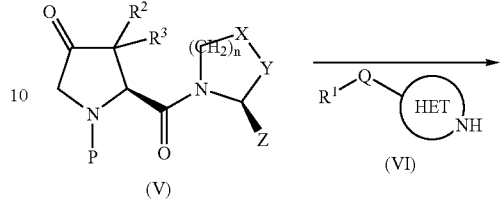
(V)      (VI)

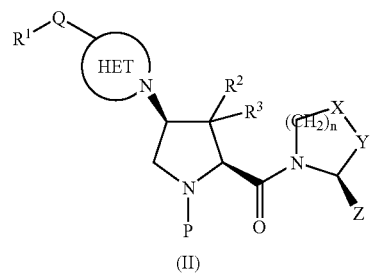
(II)

The coupling is typically accomplished by combining (III) and (IV) in a reaction-inert solvent, preferably an aprotic solvent such as acetonitrile, dichloromethane, DMF, THF, or chloroform. A coupling agent, such as EDC, HATU, DCC, EEDQ, CDI, pivaloyl chloride or diethylphosphorylcyanide is then added, optionally in the presence of a base, such as TEA or pyridine, and an optional adjuvant, such as HOBT or HOAT. The coupling is typically effected at a temperature of between about 0° C. and about 50° C., for a suitable time, such as from about one hour and about 24 hours, for example about 16 hours. For a discussion of other conditions useful for coupling carboxylic acids see Houben-Weyl, Vol. XV, Part II, E. Wunsch, Ed., G. Theime Verlag, (1974), Stuttgart; M. Bodansky, "Principles of Peptide Synthesis", Springer-Verlag Berlin (1984); and "The Peptides: Analysis, Synthesis and Biology" (ed. E. Gross and J. Meienhofer), Vols. 1-5 (Academic Press NY 1979-1983). The compounds of formulae (Ill) and (IV) may be prepared by known methods or, alternatively, according to the exemplary preparative procedures described hereinbelow. For exemplary preparations of formula (IV) amines, see PCT International Application Publication No. WO 2003/101958 and U.S. Pat. No. 6,710,040, the disclosure of which is incorporated herein by reference.

Alternatively, the compounds of formula (II) may be prepared as described below in Scheme 3.

In Scheme 3, the compounds of formula (II) are prepared by reductive amination of a protected ketone (V), prepared as described hereinbelow in Scheme 4, with an appropriately-substituted heterocycloalkylamine (VI). Such amination reactions are well-known to one skilled in the art. See, for example, A. F. Abdel-Magid, et al., J. Org. Chem., 61, 3849 (1996); R. F. Borch, et al., J. Am. Chem. Soc., 93, 2897 (1971); and S. Bhattacharyya, et al., Synlett, 1079 (1995). The formula (VI) amines are well-known in the relevant art and may be obtained commercially or prepared by known methods. See, for example, D. A. Horton, et al., Chem. Rev., 103, 893-930 (2003), H. Fukui, et al, Heterocycles, 56, 257-264 (2002), M. Y. Chu-Moyer, et al., J. Org. Chem., 60, 5721-5725 (1995), and J. P. Yevich, et al., J. Med. Chem., 29, 359-369 (1986).

Typically, (V) and (VI) are condensed in the presence of a reducing agent such as sodium borohydride, sodium cyanoborohydride, sodium triacetoxyborohydride, tetramethylammonium triacetoxyborohydride, or hydrogen in the presence of a catalyst (10% Pd/C, platinum oxide, etc.), optionally in the presence of an acid (e.g. acetic acid (AcOH), hydrochloric acid, etc.). The coupling is normally effected in a reaction-inert solvent, such as 1,2-dichloroethane, THF, DMF, EtOH, or MeOH. The reaction is performed at a suitable temperature, such as 0 to 50° C., for a suitable period of time, such as between about one to about 24 hours, for example, about 16 hours.

The compounds of formula (V) may be prepared as described hereinbelow in Scheme 4, beginning with, as appropriate, commercially available carboxylic acid (VII), ketocarboxylic acid (IX), or ketoester (X).

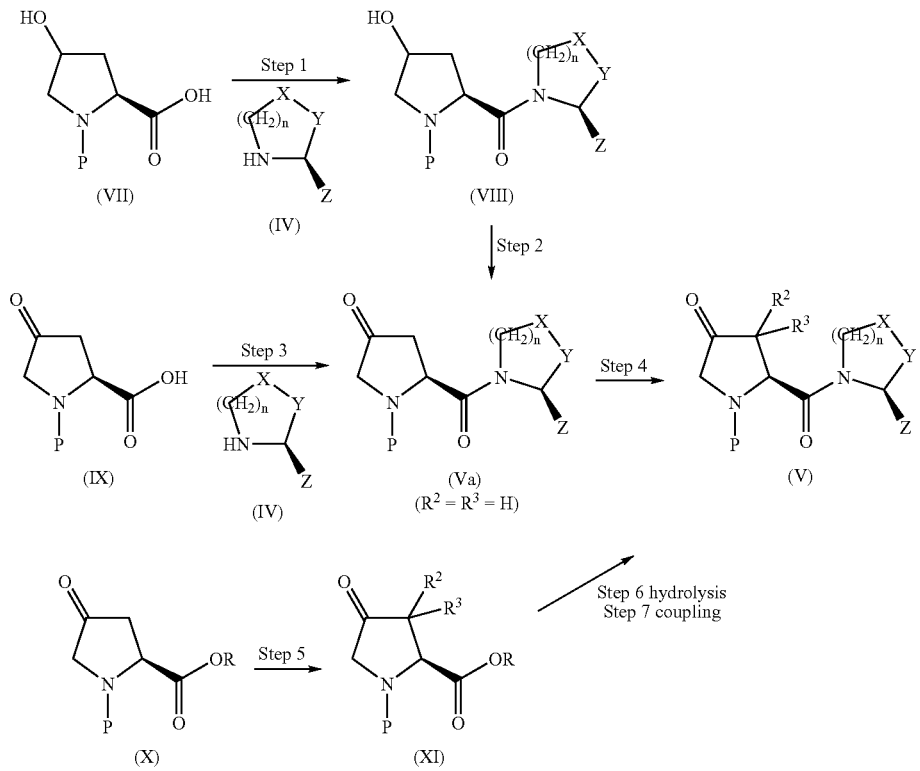

Scheme 4

In Scheme 4, Step 1, protected acid (VII) is coupled with amine (IV) as described hereinabove in Scheme 2 to afford alcohol (VIII).

In Scheme 4, Step 2, alcohol (VIII) is oxidized to ketone (Va) by treating (VIII) with an oxidizing agent in a reaction-inert solvent. Examples of appropriate oxidizing agents comprise pyridine/sulfur trioxide in DMSO; aqueous sodium hypochlorite in the presence of sodium bromide and TEMPO (2,2,6,6-tetramethyl-1-piperidinyloxy) free radical catalyst; chromium based reagents, such as chromium trioxide, pyridinium dichromate, or pyridinium chlorochromate; and oxalyl chloride in DMSO in the presence of a tertiary amine. Examples of reaction-inert solvents comprise dichloromethane, EtOAc, toluene, or pyridine. The oxidation is typically conducted at a temperature of between about −78° C. and about 50° C., for between about one and about 24 hours, for example, about 16 hours. Such oxidations are well-known to one skilled in the art. See, for example, M. Tampa, et al., J. Org. Chem., 66, 3593 (2001) and X-I. Qiu, et al., J. Org. Chem., 67, 7162 (2002).

In Scheme 4, Step 3, protected ketocarboxylic acid (IX) is first coupled with amine (IV), as described hereinabove in Scheme 2, to afford (Va), which is then alkylated to afford ketone (V). The alkylation is typically effected by first forming an enamine by reacting ketone (Va) with a secondary amine, for example, pyrrolidine, piperidine or morpholine, followed by treatment with an alkylating agent, optionally in the presence of a base, such as potassium carbonate. Typically, the reaction is effected in a solvent such as benzene, toluene, acetonitrile, or dioxane. Such conversions are well-known to one skilled in the art. See, for example, G. Stork, et al., J. Am. Chem. Soc., 85, 207 (1963); M. W. Holladay, et al., J. Med. Chem., 34, 455 (1991); and P. Barraclough, et al., Tetrahedron, 51, 4195 (1995).

In Scheme 4, Step 5, protected ketoester (X), wherein R represents an alkyl or arylalkyl moiety, is alkylated under the conditions previously described in Step 4 to afford ketoester (XI).

In Scheme 4, Step 6, ketoester (XI) is saponified to yield the corresponding carboxylic acid which, in Step 7, is coupled with an appropriately-substituted amine (IV), as previously described hereinabove in Scheme 2. The saponification step is typically accomplished by dissolving (XI) in a water-miscible solvent, such as MeOH or EtOH, and water in the presence of a base, such as lithium hydroxide or sodium hydroxide. The saponification is effected at suitable temperature, such as between about 0° C. and about 100° C., preferably room temperature, for a suitable time, such as between about one and about 24 hours, for example, about 16 hours.

Preferably, a pharmaceutical composition of the present invention comprises a therapeutically effective amount of a compound of Formula (IA), or a prodrug thereof, or a pharmaceutically acceptable salt of the compound or prodrug, or a solvate of the compound, prodrug or salt, and a pharmaceutically acceptable carrier, vehicle, diluent or excipient.

More preferably, a pharmaceutical composition of the present invention comprises a therapeutically effective amount of the compound (3,3-difluoropyrrolidin-1-yl)-((2S, 4S)-4-(4-(pyrimidin-2-yl)piperazin-1-yl)pyrrolidin-2-yl) methanone, or a prodrug thereof, or a pharmaceutically acceptable salt of said compound or prodrug, or a solvate of said compound, prodrug or salt; and a pharmaceutically acceptable carrier, vehicle, diluent or excipient.

The pharmaceutical compositions formed by combining the compounds of this invention and the pharmaceutically acceptable carriers, vehicles or diluents are then readily administered in a variety of dosage forms such as tablets, powders, lozenges, syrups, injectable solutions and the like. These pharmaceutical compositions can, if desired, contain additional ingredients such as flavorings, binders, excipients and the like.

Thus, for purposes of oral administration, tablets containing various excipients such as sodium citrate, calcium carbonate and/or calcium phosphate, may be employed along with various disintegrants such as starch, alginic acid and/or certain complex silicates, together with binding agents such as polyvinylpyrrolidone, sucrose, gelatin and/or acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the active pharmaceutical agent therein may be combined with various sweetening or flavoring agents, coloring matter or dyes and, if desired, emulsifying or suspending agents, together with diluents such as water, ethanol, propylene glycol, glycerin and/or combinations thereof.

For parenteral administration, solutions of the compounds or compositions of this invention in sesame or peanut oil, aqueous propylene glycol, or in sterile aqueous solutions may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, the sterile aqueous media employed are all readily available by standard techniques known to those skilled in the art.

For intranasal administration or administration by inhalation, the compounds or compositions of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of a compound of this invention. Capsules and cartridges (made, for example, from gelatin) for use in an inhaler or insufflator may be formulated containing a powder mix of a compound or compounds of the invention and a suitable powder base such as lactose or starch.

Methods of preparing various pharmaceutical compositions with a certain amount of active ingredient are known, or will be apparent in light of this disclosure, to those skilled in this art. For examples of methods of preparing pharmaceutical compositions, see Remington's Pharmaceutical Sciences, Mack Publishing Company, Easton, Pa., 19th Edition (1995).

In another aspect, the invention is directed to a pharmaceutical composition, which comprises a therapeutically effective amount of a first compound of Formula (I), a prodrug thereof or a pharmaceutically acceptable salt of the compound or the prodrug; a second compound that is an antidiabetic agent selected from insulin and insulin analogs; insulinotropin; biguanides; $\alpha_2$-antagonists and imidazolines; glitazones; aldose reductase inhibitors; glycogen phosphorylase inhibitors; sorbitol dehydrogenase inhibitors; fatty acid oxidation inhibitors; $\alpha$-glucosidase inhibitors; $\beta$-agonists; phosphodiesterase inhibitors; lipid-lowering agents; antiobesity agents; vanadate and vanadium complexes and peroxovanadium complexes; amylin antagonists; glucagon antagonists; growth hormone secretagogues; gluconeogenesis inhibitors; somatostatin analogs; antipolytic agents; a prodrug of the antidiabetic agents, or a pharmaceutically acceptable salt of the antidiabetic agents and the prodrugs.

In another aspect, the invention is directed to a kit comprising: a first dosage form comprising a compound of Formula (I), or a prodrug thereof, or a pharmaceutically acceptable salt of the compound or prodrug, or a solvate of the compound, prodrug or salt; and a second dosage form comprising an antidiabetic agent selected from insulin and insulin analogs; insulinotropin; biguanides; $\alpha_2$-antagonists and imidazolines; glitazones; aldose reductase inhibitors; glycogen phosphorylase inhibitors; sorbitol dehydrogenase inhibitors; fatty acid oxidation inhibitors; $\alpha$-glucosidase inhibitors; $\beta$-agonists; phosphodiesterase inhibitors; lipid-lowering agents; antiobesity agents; vanadate and vanadium complexes and peroxovanadium complexes; amylin antagonists; glucagon antagonists; growth hormone secretagogues; gluconeogenesis inhibitors; somatostatin analogs; antipolytic agents; prodrugs of the antidiabetic agents, or a pharmaceutically acceptable salts of the antidiabetic agents and the prodrug; and a container for containing said first dosage (a) and said second dosage (b). In a preferred embodiment of the kit, both the first and the second dosage forms independently comprise a pharmaceutically acceptable carrier or diluent.

In another aspect, the invention is directed to a therapeutic method of inhibiting dipeptidyl peptidase-IV comprising administering to a mammal in need of such treatment a therapeutically effective amount of a compound of Formula (I), or a prodrug thereof, or a pharmaceutically acceptable salt of the compound or of the prodrug, or a solvate of the compound, prodrug or salt; either alone or in combination with an antidiabetic agent as described above.

In another aspect, the invention is directed to a method of treating a condition mediated by dipeptidyl peptidase-IV inhibition comprising administering to a mammal in need of such treatment a therapeutically effective amount of a compound of Formula (I), or a prodrug thereof, or a pharmaceutically acceptable salt of the compound or of the prodrug, or a solvate of the compound, prodrug or salt; either alone or in combination with an antidiabetic agent as described above.

In one embodiment, the condition treated is Type 2 diabetes, Type 1 diabetes, impaired glucose tolerance, hyperglycemia, metabolic syndrome (syndrome X and/or insulin resistance syndrome), glucosuria, metabolic acidosis, arthritis, cataracts, diabetic neuropathy, diabetic nephropathy, diabetic retinopathy, diabetic cardiomyopathy, obesity, conditions exacerbated by obesity, hypertension, hyperlipidemia, atherosclerosis, osteoporosis, osteopenia, frailty, bone loss, bone fracture, acute coronary syndrome, short stature due to growth hormone deficiency, infertility due to polycystic ovary syndrome, anxiety, depression, insomnia, chronic fatigue, epilepsy, eating disorders, chronic pain, alcohol addiction, diseases associated with intestinal motility, ulcers, irritable bowel syndrome, inflammatory bowel syndrome; short bowel syndrome; and the prevention of disease progression in Type 2 diabetes.

In a preferred embodiment, the condition treated is Type 2 diabetes.

In another aspect, the invention is directed to a method of identifying an insulin secretagogue agent for diabetes, comprising: administering an agent of Formula (I) to a fasted, diabetic KK/H1J symptomatic mouse; and assessing a response in the mouse to a subsequent oral glucose challenge, wherein, if said mouse demonstrates an improvement in the symptoms, said agent is identified as a treatment for Type 2 diabetes, Type 1 diabetes, impaired glucose tolerance, hyperglycemia, metabolic syndrome (syndrome X and/or insulin resistance syndrome), glucosuria, metabolic acidosis, arthritis, cataracts, diabetic neuropathy, diabetic nephropathy, diabetic retinopathy, diabetic cardiomyopathy, obesity, conditions exacerbated by obesity, hypertension, hyperlipidemia, atherosclerosis, osteoporosis, osteopenia, frailty, bone loss, bone fracture, acute coronary syndrome, short stature due to growth hormone deficiency, infertility due to polycystic ovary syndrome, anxiety, depression, insomnia, chronic fatigue, epilepsy, eating disorders, chronic pain, alcohol addiction, diseases associated with intestinal motility, ulcers, irritable bowel syndrome, inflammatory bowel syndrome; short bowel syndrome, and to prevent disease progression in Type 2 diabetes.

The present invention also relates to therapeutic methods for treating or preventing the above described conditions in a mammal, including a human, wherein a compound of Formula (I) of this invention is administered as part of an appropriate dosage regimen designed to obtain the benefits of the therapy. The appropriate dosage regimen, the amount of each dose administered and the intervals between doses of the compound will depend upon the compound of Formula (I) of this invention being used, the type of pharmaceutical compositions being used, the characteristics of the subject being treated and the severity of the conditions.

In general, an effective dosage for the compounds of the present invention is in the range of 0.01 mg/kg/day to 30 mg/kg/day, preferably 0.01 mg/kg/day to 5 mg/kg/day of active compound in single or divided doses. Some variation in dosage will necessarily occur, however, depending on the condition of the subject being treated. The individual responsible for dosing will, in any event, determine the appropriate dose for the individual subject. Practitioners will appreciate that "kg" refers to the weight of the patient measured in kilograms.

The compounds or compositions of this invention may be administered in single (e.g., once daily) or multiple doses or via constant infusion. The compounds of this invention may also be administered alone or in combination with pharmaceutically acceptable carriers, vehicles or diluents, in either single or multiple doses. Suitable pharmaceutical carriers, vehicles and diluents include inert solid diluents or fillers, sterile aqueous solutions and various organic solvents.

The compounds or compositions of the present invention may be administered to a subject in need of treatment by a variety of conventional routes of administration, including orally and parenterally, (e.g., intravenously, subcutaneously or intramedullary). Further, the pharmaceutical compositions of this invention may be administered intranasally, as a suppository, or using a "flash" formulation, i.e., allowing the medication to dissolve in the mouth without the need to use water.

EXEMPLIFICATION

Unless noted otherwise, all reactants were obtained commercially.

Flash chromatography was performed according to the method described by W. C. Still et al. in *J. Org. Chem.* 1978, 43, 2923.

PREPARATIVE EXPERIMENTAL

The compounds and intermediates of the present invention were generally named according to the IUPAC (International Union for Pure and Applied Chemistry) recommendations on Nomenclature of Organic Chemistry and the CAS Index rules.

Preparation 1 tert-butyl-(2S)-2-[(3,3-Difluoropyrrolidin-1-yl)carbonyl]-4-oxopyrrolidine-1-carboxylate Step 1—tert-butyl-(2S,4R)-2-[(3,3-Difluoropyrrolidin-1-yl)carbonyl]-4-hydroxypyrrolidine-1-carboxylate TEA (0.77 mL, 5.5 mmol) was added to a suspension of 3,3-difluoropyrrolidine hydrochloride (0.79 g, 5.5 mmol; Synlett, 55 (1995)), in 10 mL of dichloromethane. After five min, (4R)-1-(tert-butoxycarbonyl)-4-hydroxy-L-proline (1.16 g, 5 mmol), HOBt (0.74 g, 5.5 mmol), and EDC (1.05 g, 5.5 mmol) were added. After stirring the reaction overnight, the mixture was washed sequentially with saturated sodium bicarbonate and brine, dried over magnesium sulfate, filtered, and concentrated. The residue was purified by chromatography (Biotage® Flash 40S (A Dynax Corp.; Charlottesville, Va.), 9:1 dichloromethane:methanol) to afford 1.07 g of a light pink foam. Additional product (0.26 g) was obtained by repeated dichloromethane extractions of the aqueous layer to provide an overall yield of 1.33 g (83%). MS m/z 321 (MH$^+$).

Step 2

DMSO (0.57 mL, 8 mmol) in 3 mL dichloromethane was added dropwise to a solution of oxalyl chloride (0.38 mL, 4.4 mmol) in 10 mL dichloromethane at −65° C. After five min, a solution of the product of Step 1 (1.28 g, 4 mmol) in 20 mL dichloromethane was added. After 15 min, TEA (2.79 mL, 20 mmol) was added. The reaction mixture was allowed to warm to RT. After 2 hr, the mixture was poured onto ice. The organic layer was separated, washed sequentially with 10% NaHCO$_3$ solution and brine, dried (MgSO$_4$), and concentrated. The residue was purified by chromatography (Biotage® Flash 40S, 95:5 dichloromethane:MeOH) to afford 765 mg (60%) of the title compound. MS m/z 319 (MH$^+$).

Alternatively, tert-butyl-(2S)-2-[(3,3-difluoropyrrolidin-1-yl)carbonyl]-4-oxopyrrolidine-1-carboxylate may be prepared according to the following procedure.

1-(tert-Butoxycarbonyl)-4-oxo-L-proline (6.88 g, 30 mmol), HOBt (4.46 g, 33 mmol), EDC (6.326 g, 33 mmol), and 3,3-difluoropyrrolidine hydrochloride (4.52 g, 31.5 mmol) were dissolved in 100 mL of dichloromethane and the reaction mixture was cooled to 0° C. in an ice bath before adding TEA (8.4 mL, 60 mmol). The reaction mixture was then allowed to warm to RT. After stirring overnight, saturated sodium bicarbonate (100 mL) was added and the aqueous layer was extracted with dichloromethane. The combined organic layers were washed with brine, dried over magnesium sulfate, filtered, and concentrated. The residue was purified by chromatography (Biotage® Flash 40M, eluting with 1:10 dichloromethane:hexanes) to afford the title compound 7.85 g (82% yield). MS (EI) m/z 319.3 (MH$^+$).

Preparation 2 tert-Butyl (2)-2-{[(3R*,4S)-3,4-difluoropyrrolidin-1-yl]carbonyl}-4-oxopyrrolidine-1-carboxylate Step 1—tert-Butyl (2S,4R)-2-{[(3R*,4S*)-3,4-difluoropyrrolidin-1-yl]carbonyl}-4-hydroxypyrrolidine-1-carboxylate (4R)-1-(tert-butoxycarbonyl)-4-hydroxy-L-proline (2.31 g, 10 mmol), was coupled with (3R,4S)-rel-3,4-difluoropyrrolidine hydrochloride (1.44 g, 10 mmol, Preparation 4), in a manner analogous to that described in Preparation 1, Step 1, to afford 2.15 g (67%) of the title product as an off-white foam. MS m/z 321 (MH$^+$).

Step 2

The product of Step 1 (1.97 g, 6.15 mmol) was oxidized in a manner analogous to that described in Preparation 1, Step 2, to afford 0.74 g (38%) of the title compound as a light yellow solid. MS m/z 319 (MH$^+$).

Preparation 3

(4S)-1-(tert-Butoxycarbonyl)-4-(4-pyrimidin-2-ylpiperazin-1-yl)-L-proline 1-(tert-Butoxycarbonyl)-4-oxo-L-proline (1.0 g, 4.4 mmol), 2-piperazin-1-ylpyrimidine (0.73 g, 4.4 mmol), and acetic acid (275 µL, 4.6 mmol) were dissolved in 20 mL of anhydrous 1,2-dichloroethane and sodium triacetoxyborohydride (1.85 g, 8.7 mmol) was added. After agitating at RT for 24 hr, the reaction mixture was quenched with saturated NaHCO$_3$. The pH was adjusted to pH 7 by addition of solid NaHCO$_3$ and concentrated HCl, the mixture was extracted with dichloromethane, dried over MgSO$_4$, filtered, and concentrated to afford 1.0 (61%) of crude material that was sufficiently pure for further use. MS m/z 378 (MH$^+$).

Preparation 4

(3R,4S)-rel-3,4-Difluoro-pyrrolidine hydrochloride

Step 1—2,5-Dihydro-pyrrole-1-carboxylic acid benzyl ester

3-Pyrroline (10 g, 0.145 mol) was added to a slurry of sodium bicarbonate (14 g, 0.17 mol) in toluene (100 mL). The mixture was cooled to 0° C. and benzyl chloroformate (23 mL, 0.16 mol) was added dropwise. After stirring overnight the solution was diluted with dichloromethane, washed with cold water and brine, dried over magnesium sulfate, and concentrated to a pale yellow oil that was distilled in vacuo. Bp 119-126° C. (0.32 mm).

Step 2—6-Oxa-3-aza-bicyclo[3.1.0]hexane-3-carboxylic acid benzyl ester

The title compound of Step 1 (3.0 g, 15 mmol) was dissolved in a mixture of acetonitrile (100 mL) and water (70 mL) containing ethylenediamine tetraacetate, disodium salt dihydrate (11 mg, 0.03 mmol). The solution was cooled to 0° C. and 1,1,1-trifluoroacetone (14.5 mL, 160 mmol) was added over 10 min. Potassium peroxymonosulfate (45 g, 74 mmol) was added portionwise over 40 min while maintaining the pH at 7 by adding sodium bicarbonate. The mixture was stirred at 0° C. for 1.5 hr then poured into water and extracted with dichloromethane. The combined extracts were dried over magnesium sulfate and concentrated to a colorless oil (3.45 g, 100%).

Step 3—(3RS,4RS)-3-Fluoro-4-hydroxy-pyrrolidine-1-carboxylic acid benzyl ester

A mixture of TEA trihydrofluoride (1.95 mL, 12 mmol) and the title compound of Step 2 (2.62 g, 12 mmol) was heated to 155° C. for three hr, cooled, and partitioned between water and dichloromethane. The aqueous phase was extracted again with dichloromethane and the combined organic extracts were washed with brine, dried over magnesium sulfate and concentrated. The residue was purified by flash-chromatography (1% methanol in dichloromethane) to give the title compound as a pale oil (1.14 g, 40%).

Step 4—(3R,4S)-rel-3,4-Difluoro-pyrrolidine-1-carboxylic acid benzyl ester

A solution of the title compound of Step 3 in dichloromethane (15 mL) was cooled to −50° C. and [bis(2-methoxyethyl)amino]sulfur trifluoride (1.3 mL, 6.9 mmol) was added. The solution was warmed to room temperature over 18 hr then partitioned between water and EtOAc. The aqueous phase was extracted again with EtOAc and the combined organic extracts were washed with brine, dried over magnesium sulfate, and concentrated. The residue was purified by flash-chromatography (dichloromethane) to give the product as a brown oil (1.14 g, 40%).

Step 5

A solution of the title compound of Step 4 (675 mg, 2.8 mmol) in EtOH (10 mL) containing 10% Pd/C (200 mg) was hydrogenated at 40 psi in a Parr apparatus for 18 hr. The solution was filtered over diatomaceous earth and the filtrate was concentrated to dryness, leaving a yellow solid (400 mg, 100%).

Preparation 5

(S)-2-(3-Fluoro-azetidine-1-carbonyl)-4-oxo-pyrrolidine-1-carboxylic acid tert-butyl ester Step 1—Benzhydryl-3-fluoro-azetidine hydrochloride 1-Benzhydryl-azetidin-3-ol (5.0 g, 20.9 mmol) was dissolved in 50 mL of benzene, the solution cooled to 15° C., and (diethylamino)sulfur trifluoride (10.1 g, 62.7 mmol) was added dropwise. After stirring overnight at room temperature, saturated sodium bicarbonate was added. The mixture was extracted with EtOAc, dried over magnesium sulfate, filtered, and concentrated. The residue was purified by chromatography (Biotage® 40S, 10% EtOAc/hexanes). The product was dissolved in EtOAc, treated with HCl (15 mL, 2N in ether), heated briefly, and concentrated. The solid was triturated with ether, filtered, and dried to provide 2.58 g of the title compound. MS m/z 242.3 (MH$^+$).

Step 2—3-Fluoro-azetidine hydrochloride

A solution of the product of Step 1 (2.58 g, 9.3 mmol) in 30 mL of methanol containing 10% Pd/C (0.38 g) was hydrogenated at 30-50 psi in a Parr apparatus for 60 hr. The solution was filtered over diatomaceous earth and the filtrate concentrated to dryness. The solid was recrystallized from MeOH/EtOAc to furnish 0.62 g (60%) of the title compound.

Step 3

N-tert-Boc-4-oxo-L-proline (917 mg, 4 mmol), the title compound of Step 2 (446 mg, 4 mmol), and HATU (1.673 g, 4.4 mmol) were mixed under nitrogen in anhydrous methylene chloride. The solution was cooled in an ice bath before the addition of DIEA (1.4 mL, 8 mmol). The reaction mixture was allowed to warm to RT and stirred overnight. Saturated sodium bicarbonate was added, the phases were separated and the aqueous phase was extracted with methylene chloride. The combined organic portions were washed with brine and dried over magnesium sulfate. The crude product (2.11 g) was purified by chromatography (Biotage® Flash 40S, 95:5 EtOAc:MeOH) to give the title product as light pink foam (1.06 g, 92%). MS m/z 287.3 (MH$^+$).

Preparation 6

(S)-2-((S)-3-Fluoro-pyrrolidine-1-carbonyl)-4-oxo-pyrrolidine-1-carboxylic acid tert-butyl ester N-tert-Boc-4-oxo-L-proline (2.29 g, 10 mmol), (S)-3-fluoropyrrolidine hydrochloride (1.38 g, 11 mmol) and TEA (2.09 mL, 15 mmol) were mixed in anhydrous methylene chloride (30 mL) under nitrogen. HOBT (2.03 g, 15 mmol) was added and the mixture cooled to 0° C. in an ice bath before addition of EDC (2.10, 11 mmol). The reaction mixture was allowed to warm to RT and stirred overnight. The mixture was washed with saturated sodium bicarbonate and brine and dried over magnesium sulfate. The crude material (3.15 g) was recrystallized from hexane:EtOAc (2:1) to give the title compound as light yellow needles (2.18 g, 73%). MS m/z 301.3 (MH$^+$).

Preparation 7

(2S,4S)-2-(3,3-Difluoro-pyrrolidine-1-carbonyl)-4-piperazin-1-yl-pyrrolidine-1-carboxylic acid tert-butyl ester Step 1—4-[(3S,5S)-1-tert-Butoxycarbonyl-5-(3,3-difluoro-pyrrolidine-1-carbonyl)-pyrrolidin-3-yl]-piperazine-1-carboxylic acid benzyl ester To a solution of the title compound of Preparation 1 (1.59 g, 5 mmol) and 1-(benzyloxycarbonyl)piperazine (1.21 g, 5.5 mmol) in 1,2-dichloroethane (20 mL) was added AcOH (0.3 mL, 1.05 equiv.), followed by sodium triacetoxyborohydride (2.119 g, 10 mmol). The reaction mixture was stirred at RT for 4 hr. Saturated sodium bicarbonate was added and the product extracted with methylene chloride.

The organic phase was washed with brine and dried over magnesium sulfate. After evaporation, the crude product (2.28 g yellow foam) was purified by flash chromatography eluting with EtOAc to give title compound as white foam (1.28 g, 49%). MS m/z 523.3 (MH$^+$).

Step 2

The product of Step 1 (1 g, 1.91 mmol) was dissolved in EtOH (50 mL) and 10% Pd/C (1 g, 1 equiv. w/w) was carefully added, followed by 1,4-cyclohexadiene (1.81 mL, 10 equiv.). The mixture was stirred gently in a tightly-capped flask at RT overnight. The reaction mixture was filtered through diatomaceous earth and concentrated to give the product as yellow semisolid (758 mg, 100%). MS m/z 389.4 (MH$^+$).

Preparation 8

(S)-2-(3,3-Difluoro-azetidine-1-carbonyl)-4-oxo-pyrrolidine-1-carboxylic acid tert-butyl ester N-tert-BOC-4-oxo-L-proline (458 mg, 2 mmol), 3,3-difluoroazetidine hydrochloride (258 mg, 2 mmol) (prepared as described in WO 2000/47582), and DIPEA (0.35 mL, 2 mmol) were mixed in anhydrous methylene chloride (10 mL) and cooled to 0° C. HOBT (405 mg, 3 mmol) was then added in one portion followed by EDC hydrochloride (422 mg, 2.2 mmol). The resulting mixture was allowed to warm to RT and stirred overnight. Saturated sodium bicarbonate was added, the organic layer was separated, and the aqueous phase extracted with methylene chloride. The combined organic extracts were washed twice with brine, dried over magnesium sulfate, filtered, and concentrated. The crude product (570 mg) was triturated with hexanes:methylene chloride (10:1), filtered, and dried in a vacuum oven to afford 510 mg (84% yield) of the title product as a light orange powder. MS (m/z): 305.1 (MH$^+$).

Preparation 9

(2S,4S)-4-Fluoro-pyrrolidine-2-carbonitrile hydrochloride

Step 1—(2S,4S)-4-Fluoro-pyrrolidine-1,2-dicarboxylic acid 2-tert-butyl ester 1-(2,5-dioxo-pyrrolidin-1-yl)ester To a solution of N-tert-BOC-cis-4-fluoro-L-proline (700 mg, 3 mmol) in anhydrous DMF (8 mL) was at 0° C. added N-hydroxysuccinimide (380 mg, 3.3 mmol) in one portion, followed by 1,3-diisopropylcarbodiimide (391 mg, 3.1 mmol) in small portions. The reaction was allowed to warm to RT and stirred overnight. The mixture was diluted with 100 mL of water, the precipitate was collected, washed with cold water, and dried in a vacuum oven overnight. The product (1.093 g) was used without further purification. MS m/z 331.3 (MH$^+$).

Step 2—(2S,4S)-2-Carbamoyl-4-fluoro-pyrrolidine-1-carboxylic acid tert-butyl ester The title compound of Step 1 (1.03 g, 3.12 mmol) was dissolved in dioxane (12 mL) at RT and the solution was treated with concentrated aqueous ammonium hydroxide (10 mmol) dropwise. The resulting thick solution was stirred at RT for three hr, then acidified with 6N HCl to pH 4-5, and extracted with methylene chloride (2×). The combined extracts were washed with saturated sodium bicarbonate and brine, dried over magnesium sulfate, filtered, and concentrated to afford 562 mg (78% yield) of a clear oil. MS m/z 233.3 (MH+).

Step 3—(2S,4S)-2-Cyano-4-fluoro-pyrrolidine-1-carboxylic acid tert-butyl ester

To a solution of the title compound of Step 2 (550 mg, 2.37 mmol) and dry pyridine (0.4 mL, 2 equiv.) in anhydrous methylene chloride (15 mL) at 0° C. was added a solution of TFAA in 2 mL of methylene chloride under nitrogen. The solution was stirred at 0° C. for two hr and then at RT for one hr. The reaction mixture was washed with saturated aqueous sodium bicarbonate and brine, dried over magnesium sulfate, filtered, and concentrated. The residue was purified by flash chromatography on silica gel to give 458 mg (90% yield) of an oil that solidified on standing. MS m/z 215.3 (MH+).

Step 4

The title compound of Step 3 (400 mg) was dissolved in dry acetonitrile (8 mL) and 0.5 mL of 4N HCl in dioxane was added under nitrogen. The resulting solution was stirred at RT overnight and the white precipitate that formed was filtered and dried in a vacuum oven to yield 128 mg (46% yield) of the title compound. MS m/z 115.1 (MH+). Additional product could be obtained from the filtrate.

Preparation 10

(2S)-4,4-Difluoro-pyrrolidine-2-carbonitrile hydrochloride

Step 1—N-tert-BOC-4,4-Difluoropyrrolidine-2-carbonitrile

To a solution of N-tert-BOC-4,4-difluoropyrrolidine-L-proline amide (250 mg, 1 mmol) and dry pyridine (97 µL, 1.2 equiv.) in anhydrous methylene chloride at 0° C. was added a solution of TFAA (252 mg, 1.2 equiv.) in 1 mL of anhydrous methylene chloride. The solution was allowed to warm to RT and stirred for 36 hr. The reaction was quenched with saturated ammonium chloride, the organic phase was washed successively with 1N HCl, saturated sodium bicarbonate and brine, dried over magnesium sulfate, filtered, and concentrated to afford 252 mg of a white semisolid. MS m/z 233.1 (MH+).

Step 2

The title compound of Step 1 (245 mg) was dissolved in dry acetonitrile (10 mL) and 0.5 mL of 4N HCl was added. The resulting solution was stirred at RT for five hr and the solvents were removed. The residue was triturated with EtOAc, the solid was filtered, and then dried under high-vacuum to afford 105 (59% yield) of the title compound as a white solid. MS m/z 133.2 (MH+).

The compounds of formula (I), the stereoisomers thereof, and the pharmaceutically acceptable salts of the compounds and stereoisomers, may be prepared as described in the following Examples. The free base compounds of the present invention may be obtained from their salt forms by conventional means such as disclosed in Example 113, herein.

EXAMPLE 1

((2S,4S)-4-(4-(3-(Trifluoromethyl)phenyl)piperazin-1-yl)pyrrolidin-2-yl)-(3,3-difluoropyrrolidin-1-yl)-methanone dihydrochloride Step 1—tert-Butyl (2S,4S)-2-[(3,3-difluoropyrrolidin-1-yl)carbonyl]-4-{4-[3-(trifluoromethyl)phenyl]piperazin-1-yl}pyrrolidine-1-carboxylate The title compound of Preparation 1 (96 mg, 0.3 mmol), 1-[3-(trifluoromethyl)phenyl]piperazine (70 mg, 0.3 mmol) and AcOH (18 µL, 0.3 mmol) were dissolved in 8 mL anhydrous 1,2-dichloroethane. Sodium triacetoxyborohydride (127 mg, 0.6 mmol) was added. After stirring the reaction at RT for 3 hr, the reaction was quenched with saturated sodium bicarbonate, extracted with EtOAc, washed with brine, dried over magnesium sulfate, filtered, and concentrated. The crude material was purified by chromatography (Biotage® Flash 40S, 95:5 dichloromethane:MeOH) to afford 126 mg (79%) of the title compound as a white foam. MS m/z 533 (MH+).

Step 2

The product of Step 1 (120 mg, 0.225 mmol) was treated with 4N HCl in dioxane (5 mL). After two hr at RT, the mixture was concentrated to dryness, triturated with ether, filtered, and dried in vacuo to provide 92 mg of the title compound as a white solid. MS m/z 433 (MH+).

Using appropriate starting materials, the hydrochloride salts of the compounds of Examples 2 to 112, disclosed in Table 1 hereinbelow, were prepared in a manner analogous to that described in Example 1.

TABLE 1

| Example | Name | MS (M + 1) |
|---|---|---|
| 2 | ((2S,4S)-4-(4-(5-(Trifluoromethyl)pyridin-2-yl)piperazin-1-yl)pyrrolidin-2-yl)-(3,3-difluoropyrrolidin-1-yl)-methanone | 434 |
| 3 | ((2S,4S)-4-(4-(5-(Trifluoromethyl)pyridin-2-yl)-1,4-diazepan-1-yl)pyrrolidin-2-yl)-(3,3-difluoropyrrolidin-1-yl)-methanone | 448 |
| 4 | ((2S,4S)-4-(4-(3-(Trifluoromethyl)phenyl)piperazin-1-yl)pyrrolidin-2-yl)-((3R*,4S*)-3,4-difluoropyrrolidin-1-yl)-methanone | 433 |
| 5 | ((2S,4S)-4-(4-(2-(Trifluoromethyl)quinolin-4-yl)piperazin-1-yl)pyrrolidin-2-yl)-(3,3-difluoropyrrolidin-1-yl)-methanone | 484 |

TABLE 1-continued

| Example | Name | MS (M + 1) |
|---|---|---|
| 6 | (3,3-Difluoropyrrolidin-1-yl)-((2S,4S)-4-(4-(5-nitropyridin-2-yl)piperazin-1-yl)pyrrolidin-2-yl)-methanone | 411 |
| 7 | ((2S,4S)-4-(4-(3-Cyanopyridin-2-yl)piperazin-1-yl)pyrrolidin-2-yl)-(3,3-difluoropyrrolidin-1-yl)-methanone | 391 |
| 8 | ((2S,4S)-4-(4-(5-(Trifluoromethyl)pyridin-2-yl)piperazin-1-yl)pyrrolidin-2-yl)-((3R*,4S*)-3,4-difluoropyrrolidin-1-yl)-methanone | 434 |
| 9 | ((2S,4S)-4-(4-(3-Cyanopyridin-2-yl)piperazin-1-yl)pyrrolidin-2-yl)-((3R*,4S*)-3,4-difluoropyrrolidin-1-yl)-methanone | 391 |
| 10 | ((2S,4S)-4-(4-(3-Cyanopyrazin-2-yl)piperazin-1-yl)pyrrolidin-2-yl)-((3R*,4S*)-3,4-difluoropyrrolidin-1-yl)-methanone | 392 |
| 11 | ((2S,4S)-4-(4-(4-(Trifluoromethyl)phenyl)piperazin-1-yl)pyrrolidin-2-yl)-((3R*,4S*)-3,4-difluoropyrrolidin-1-yl)-methanone | 433 |
| 12 | ((2S,4S)-4-(2-(Trifluoromethyl)-5,6-dihydroimidazo[1,2-a]pyrazin-7(8H)-yl)pyrrolidin-2-yl)-((3R*,4S*)-3,4-difluoropyrrolidin-1-yl)-methanone | 394 |
| 13 | ((2S,4S)-4-(4-(3-Cyanopyrazin-2-yl)piperazin-1-yl)pyrrolidin-2-yl)-(3,3-difluoropyrrolidin-1-yl)-methanone | 392 |
| 14 | ((2S,4S)-4-(2-(Trifluoromethyl)-5,6-dihydroimidazo[1,2-a]pyrazin-7(8H)-yl)pyrrolidin-2-yl)-(3,3-difluoropyrrolidin-1-yl)-methanone | 394 |
| 15 | ((3R*,4S*)-3,4-difluoropyrrolidin-1-yl)-((2S,4S)-4-(4-(pyrimidin-2-yl)piperazin-1-yl)pyrrolidin-2-yl)-methanone | 367 |
| 16 | ((2S,4S)-4-(4-(2-(Trifluoromethyl)phenyl)piperazin-1-yl)pyrrolidin-2-yl)-(3,3-difluoropyrrolidin-1-yl)-methanone | 433 |
| 17 | ((2S,4S)-4-((1S,5R,6R)-6-Amino-3-aza-bicyclo[3.1.0]hexan-3-yl)pyrrolidin-2-yl)-(3,3-difluoropyrrolidin-1-yl)-methanone | 301 |
| 18 | ((2S,4S)-4-(4-Cyano-4-phenylpiperidin-1-yl)pyrrolidin-2-yl)-(3,3-difluoropyrrolidin-1-yl)methanone | 389 |
| 19 | (2S,4S)-4-(4-(1,1-Dioxo-1H-1,2-benzo[d]isothiazol-3-yl)-piperazin-1-yl)pyrrolidin-2-yl)-(3,3-difluoro-pyrrolidin-1-yl)-methanone | 454 |
| 20 | ((2S,4S)-4-(4-(5-(Trifluoromethyl)-1,3,4-thiadiazol-2-yl)piperazin-1-yl)pyrrolidin-2-yl)-(3,3-difluoropyrrolidin-1-yl)-methanone | 441 |
| 21 | (3,3-Difluoropyrrolidin-1-yl)-((2S,4S)-4-(4-(isothiazol-3-yl)piperazin-1-yl)pyrrolidin-2-yl)methanone | 372 |
| 22 | (3,3-Difluoropyrrolidin-1-yl)-((2S,4S)-4-(4-(8-methyl-[1,2,4]triazolo[4,3-a]pyrazin-3-yl)piperazin-1-yl)pyrrolidin-2-yl)-methanone | 421 421 |
| 23 | ((2S,4S)-4-(3-(Trifluoromethyl)-5,6-dihydro-[1,2,4]triazolo[4,3-a]pyrazin-7(8H)-yl)pyrrolidin-2-yl)-(3,3-difluoropyrrolidin-1-yl)-methanone | 395 |
| 24 | (3,3-Difluoropyrrolidin-1-yl)-((2S,4S)-4-(4-(2,6-dimethylpyrimidin-4-yl)piperazin-1-yl)pyrrolidin-2-yl)-methanone | 395 |
| 25 | ((2S,4S)-4-(4-(Benzo[d]isothiazol-3-yl)piperazin-1-yl)pyrrolidin-2-yl)-(3,3-difluoropyrrolidin-1-yl)-methanone | 422 |
| 26 | ((2S,4S)-4-(4-(4-(Trifluoromethyl)-6-methylpyridin-2-yl)piperazin-1-yl)pyrrolidin-2-yl)-(3,3-difluoropyrrolidin-1-yl)-methanone | 448 |
| 27 | (3,3-Difluoropyrrolidin-1-yl)-((2S,4S)-4-(4-(oxazolo[5,4-b]pyridin-2-yl)piperazin-1-yl)pyrrolidin-2-yl)-methanone | 407 |
| 28 | (3,3-Difluoropyrrolidin-1-yl)-((2S,4S)-4-(4-(4-methylpyrimidin-2-yl)piperazin-1-yl)pyrrolidin-2-yl)-methanone | 381 |
| 29 | ((2S,4S)-4-(4-(4-Cyanopyridin-2-yl)piperazin-1-yl)pyrrolidin-2-yl)-(3,3-difluoropyrrolidin-1-yl)-methanone | 391 |
| 30 | ((2S,4S)-4-(4-(7-(Trifluoromethyl)quinolin-4-yl)piperazin-1-yl)pyrrolidin-2-yl)-(3,3-difluoropyrrolidin-1-yl)-methanone | 484 |
| 31 | ((2S,4S)-4-(4-(5-Cyanopyridin-2-yl)piperazin-1-yl)pyrrolidin-2-yl)-(3,3-difluoropyrrolidin-1-yl)-methanone | 391 |
| 32 | (3,3-Difluoropyrrolidin-1-yl)-((2S,4S)-4-(4-(pyridin-2-yl)piperazin-1-yl)pyrrolidin-2-yl)methanone | 366 |
| 33 | ((2S,4S)-4-(4-(6-(Trifluoromethyl)quinolin-4-yl)piperazin-1-yl)pyrrolidin-2-yl)-(3,3-difluoropyrrolidin-1-yl)-methanone | 484 |
| 34 | (3,3-Difluoropyrrolidin-1-yl)-((2S,4S)-4-(4-(5-methylpyridin-2-yl)piperazin-1-yl)pyrrolidin-2-yl)-methanone | 380 |
| 35 | ((2S,4S)-4-(4-(4-(Trifluoromethyl)pyrimidin-2-yl)piperazin-1-yl)pyrrolidin-2-yl)-(3,3-difluoropyrrolidin-1-yl)-methanone | 435 |
| 36 | (3,3-Difluoropyrrolidin-1-yl)-((2S,4S)-4-(4-(3-methyl-1,2,4-oxadiazol-5-yl)piperidin-1-yl)pyrrolidin-2-yl)-methanone | 370 |
| 37 | (3,3-Difluoropyrrolidin-1-yl)-((2S,4S)-4-(4-(quinolin-2-yl)piperazin-1-yl)pyrrolidin-2-yl)-methanone | 416 |
| 38 | (3,3-Difluoropyrrolidin-1-yl)-((2S,4S)-4-(4-(6-methoxypyridin-2-yl)piperazin-1-yl)pyrrolidin-2-yl)-methanone | 396 |
| 39 | (3,3-Difluoropyrrolidin-1-yl)-((2S,4S)-4-(4-(5-methyl-1,2,4-oxadiazol-3-yl)piperidin-1-yl)pyrrolidin-2-yl)-methanone | 370 |
| 40 | (3,3-Difluoropyrrolidin-1-yl)-((2S,4S)-4-(4-(quinolin-8-yl)piperazin-1-yl)pyrrolidin-2-yl)-methanone | 416 |

TABLE 1-continued

| Example | Name | MS (M + 1) |
|---|---|---|
| 41 | (3,3-Difluoropyrrolidin-1-yl)-((2S,4S)-4-(4-(1-phenyl-1H-imidazol-2-yl)piperidin-1-yl)pyrrolidin-2-yl)-methanone | 430 |
| 42 | (3,3-Difluoropyrrolidin-1-yl)-((2S,4S)-4-(quinoxalin-5-yl)piperazin-1-yl)pyrrolidin-2-yl)-methanone | 417 |
| 43 | ((2S,4S)-4-(4-(Benzo[d]isoxazol-3-yl)piperazin-1-yl)pyrrolidin-2-yl)-(3,3-difluoropyrrolidin-1-yl)methanone | 406 |
| 44 | (3,3-Difluoro-pyrrolidin-1-yl)-[(2S,4S)-4-(8-trifluoromethyl-3,4-dihydro-1H-benzo[4,5]imidazo[1,2-a]pyrazin-2-yl)-pyrrolidin-2-yl]-methanone | 444 |
| 45 | (3,3-Difluoropyrrolidin-1-yl)-((2S,4S)-4-(4-phenylpiperidin-1-yl)pyrrolidin-2-yl)-methanone | 364 |
| 46 | ((2S,4S)-4-(4-(3-(Trifluoromethyl)phenyl)piperidin-1-yl)pyrrolidin-2-yl)-(3,3-difluoropyrrolidin-1-yl)-methanone | 432 |
| 47 | ((2S,4S)-4-(4-(3-(Trifluoromethyl)pyridin-2-yl)piperazin-1-yl)pyrrolidin-2-yl)-(3,3-difluoropyrrolidin-1-yl)-methanone | 434 |
| 48 | ((2S,4S)-4-(4-(4-(Trifluoromethyl)quinolin-2-yl)piperazin-1-yl)pyrrolidin-2-yl)-(3,3-difluoropyrrolidin-1-yl)-methanone | 484 |
| 49 | ((2S,4S)-4-(2-(Trifluoromethyl)-7,8-dihydropyrido[4,3-d]pyrimidin-6(5H)-yl)pyrrolidin-2-yl)-(3,3-difluoropyrrolidin-1-yl)-methanone | 406 |
| 50 | (3,3-Difluoropyrrolidin-1-yl)-((2S,4S)-4-(4-(4-methyl-6-phenylpyrimidin-2-yl)piperazin-1-yl)pyrrolidin-2-yl)-methanone | 457 |
| 51 | ((2S,4S)-4-(4-(1H-Benzo[d][1,2,3]triazol-1-yl)piperidin-1-yl)pyrrolidin-2-yl)-(3,3-difluoropyrrolidin-1-yl)-methanone | 405 |
| 52 | (3,3-Difluoropyrrolidin-1-yl)((2S,4S)-4-(4-(thiazol-2-yl)piperazin-1-yl)pyrrolidin-2-yl)-methanone | 372 |
| 53 | (3,3-Difluoropyrrolidin-1-yl)-((2S,4S)-4-(4-(3-methylpyridin-2-yl)piperazin-1-yl)pyrrolidin-2-yl)-methanone | 380 |
| 54 | ((2S,4S)-4-(4-(Benzo[d]oxazol-2-yl)piperazin-1-yl)pyrrolidin-2-yl)-(3,3-difluoropyrrolidin-1-yl)-methanone | 406 |
| 55 | (3,3-Difluoropyrrolidin-1-yl)-((2S,4S)-4-(4-(6-phenylpyridin-2-yl)piperazin-1-yl)pyrrolidin-2-yl)-methanone | 442 |
| 56 | (3,3-Difluoropyrrolidin-1-yl)-((2S,4S)-4-((3R,5S)-3,5-dimethyl-4-(4,6-dimethyl-1,3,5-triazin-2-yl)piperazin-1-yl)pyrrolidin-2-yl)-methanone | 424 |
| 57 | [(2S,4S)-4-(2-Cyclopropyl-7,8-dihydro-5H-pyrido[4,3-d]pyrimidin-6-yl)-pyrrolidin-2-yl]-(3,3-difluoro-pyrrolidin-1-yl)-methanone | 378.4 |
| 58 | (3,3-Difluoro-pyrrolidin-1-yl)-[(2S,4S)-4-(2-methoxy-7,8-dihydro-5H-pyrido[4,3-d]pyrimidin-6-yl)-pyrrolidin-2-yl]-methanone | 368.3 |
| 59 | (3,3-Difluoro-pyrrolidin-1-yl)-[(2S,4S)-4-(2-phenyl-7,8-dihydro-5H-pyrido[4,3-d]pyrimidin-6-yl)-pyrrolidin-2-yl]-methanone | 414.4 |
| 60 | (3,3-Difluoro-pyrrolidin-1-yl)-[(2S,4S)-4-(4-oxazolo[4,5-c]pyridin-2-yl-piperazin-1-yl)-pyrrolidin-2-yl]-methanone | 407.4 |
| 61 | (3,3-Difluoro-pyrrolidin-1-yl)-[(2S,4S)-4-(4-oxazolo[5,4-c]pyridin-2-yl-piperazin-1-yl)-pyrrolidin-2-yl]-methanone | 407.4 |
| 62 | (3,3-Difluoro-pyrrolidin-1-yl)-[(2S,4S)-4-(2,3,4,5-tetrahydro-[1,2']bipyrazinyl-4-yl)-pyrrolidin-2-yl]-methanone | 367.4 |
| 63 | {(2S,4S)-4-[4-(3,5-Dichloro-pyridin-4-yl)-piperazin-1-yl]-pyrrolidin-2-yl}-(3,3-difluoro-pyrrolidin-1-yl)-methanone | 434.2 |
| 64 | (3,3-Difluoro-pyrrolidin-1-yl)-[(2S,4S)-4-(4-quinoxalin-2-yl-piperazin-1-yl)-pyrrolidin-2-yl]-methanone | 417.4 |
| 65 | 4-[(3S,5S)-5-(3,3-Difluoro-pyrrolidine-1-carbonyl)-pyrrolidin-3-yl]-piperazine-1-sulfonic acid dimethylamide | 396.3 |
| 66 | [(2S,4S)-4-(2-Amino-7,8-dihydro-5H-pyrido[4,3-d]pyrimidin-6-yl)-pyrrolidin-2-yl]-(3,3-difluoro-pyrrolidin-1-yl)-methanone | 353.3 |
| 67 | (3,3-Difluoro-pyrrolidin-1-yl)-[(2S,4S)-4-(2-methyl-4-pyrimidin-2-yl-piperazin-1-yl)-pyrrolidin-2-yl]-methanone | 381.4 |
| 68 | (3,3-Difluoro-pyrrolidin-1-yl)-{(2S,4S)-4-[4-(5-ethyl-pyrimidin-2-yl)-piperazin-1-yl]-pyrrolidin-2-yl}-methanone | 395.4 |
| 69 | {(2S,4S)-4-[4-(5-Bromo-pyrimidin-2-yl)-piperazin-1-yl]-pyrrolidin-2-yl}-(3,3-difluoro-pyrrolidin-1-yl)-methanone | 445.4 |
| 70 | 4-[(3S,5S)-5-(3,3-Difluoro-pyrrolidine-1-carbonyl)-pyrrolidin-3-yl]-piperazine-1-carboxylic acid benzyl ester | 423.4 |
| 71 | ((2S,4S)-4-(2-(4-Chlorophenyl)-7,8-dihydropyrido[4,3-d]pyrimidin-6(5H)-yl)pyrrolidin-2-yl)(3,3-difluoropyrrolidin-1-yl)methanone | 448.4 |
| 72 | (3,3-Difluoropyrrolidin-1-yl)((2S,4S)-4-(7,8-dihydro-2-propylpyrido[4,3-d]pyrimidin-6(5H)-yl)pyrrolidin-2-yl)methanone | 382.4 |
| 73 | {(2S,4S)-4-[4-(5-Chloro-benzooxazol-2-yl)-piperazin-1-yl]-pyrrolidin-2-yl}-(3,3-difluoro-pyrrolidin-1-yl)-methanone | 440.4 |
| 74 | (3,3-Difluoro-pyrrolidin-1-yl)-[(2S,4S)-4-((2-pyridin-2-yl)-7,8-dihydro-5H-pyrido[4,3-d]pyrimidin-6-yl)-pyrrolidin-2-yl]-methanone | 415.4 |
| 75 | (3,3-Difluoro-pyrrolidin-1-yl)-[(2S,4S)-4-(2-pyridin-4-yl-7,8-dihydro-5H-pyrido[4,3-d]pyrimidin-6-yl)-pyrrolidin-2-yl]-methanone | 415.4 |

TABLE 1-continued

| Example | Name | MS (M + 1) |
|---|---|---|
| 76 | (3,3-Difluoro-pyrrolidin-1-yl)-{(2S,4S)-4-[4-(5-methyl-benzooxazol-2-yl)-piperazin-1-yl]-pyrrolidin-2-yl}-methanone | 420.4 |
| 77 | {(2S,4S)-4-[4-(6-Chloro-benzooxazol-2-yl)-piperazin-1-yl]-pyrrolidin-2-yl}-(3,3-difluoro-pyrrolidin-1-yl)-methanone | 440.4 |
| 78 | (3,3-Difluoro-pyrrolidin-1-yl)-[(2S,4S)-4-(7,8-dihydro-5H-pyrido[4,3-d]pyrimidin-6-yl)-pyrrolidin-2-yl]-methanone | 338.4 |
| 79 | ((S)-3-Fluoro-pyrrolidin-1-yl)-[(2S,4S)-4-(4-oxazolo[5,4-c]pyridin-2-yl-piperazin-1-yl)-pyrrolidin-2-yl]-methanone | 389.4 |
| 80 | 4-[(3S,5S)-5-((S)-3-Fluoro-pyrrolidine-1-carbonyl)-pyrrolidin-3-yl]-3,4,5,6-tetrahydro-2H-[1,2']bipyrazinyl-3'-carbonitrile | 374.4 |
| 81 | ((S)-3-Fluoro-pyrrolidin-1-yl)-{(2S,4S)-4-[4-(5-trifluoromethyl-pyridin-2-yl)-piperazin-1-yl]-pyrrolidin-2-yl}-methanone | 416.4 |
| 82 | ((S)-3-Fluoro-pyrrolidin-1-yl)-[(2S,4S)-4-(4-oxazolo[5,4-b]pyridin-2-yl-piperazin-1-yl)-pyrrolidin-2-yl]-methanone | 389.4 |
| 83 | 2-{4-[(3S,5S)-5-((S)-3-Fluoro-pyrrolidine-1-carbonyl)-pyrrolidin-3-yl]-piperazin-1-yl}-nicotinonitrile | 373.4 |
| 84 | ((S)-3-Fluoro-pyrrolidin-1-yl)-{(2S,4S)-4-[4-(3-trifluoromethyl-pyridin-2-yl)-piperazin-1-yl]-pyrrolidin-2-yl}-methanone | 416.5 |
| 85 | ((2S,4S)-4-(2-(Trifluoromethyl)-7,8-dihydropyrido[4,3-d]pyrimidin-6(5H)-yl)pyrrolidin-2-yl)((S)-3-fluoropyrrolidin-1-yl)methanone | 388.4 |
| 86 | ((S)-3-Fluoro-pyrrolidin-1-yl)-{(2S,4S)-4-[4-(4-methyl-pyrimidin-2-yl)-piperazin-1-yl]-pyrrolidin-2-yl}-methanone | 363.5 |
| 87 | ((S)-3-Fluoropyrrolidin-1-yl)((2S,4S)-4-(4-(pyrazin-2-yl)piperazin-1-yl)pyrrolidin-2-yl)methanone | 349.4 |
| 88 | [(2S,4S)-4-(2-Cyclopropyl-7,8-dihydro-5H-pyrido[4,3-d]pyrimidin-6-yl)-pyrrolidin-2-yl]-((S)-3-fluoro-pyrrolidin-1-yl)-methanone | 360.4 |
| 89 | ((S)-3-Fluoro-pyrrolidin-1-yl)-{(2S,4S)-4-[4-(2-trifluoromethyl-quinolin-4-yl)-piperazin-1-yl]-pyrrolidin-2-yl}-methanone | 466.5 |
| 90 | (3-Fluoroazetidin-1-yl)((2S,4S)-4-(4-(pyrazin-2-yl)piperazin-1-yl)pyrrolidin-2-yl)methanone | 335.4 |
| 91 | 4-[(3S,5S)-5-(3-Fluoro-azetidine-1-carbonyl)-pyrrolidin-3-yl]-3,4,5,6-tetrahydro-2H-[1,2']bipyrazin-3'-carbonitrile | 360.4 |
| 92 | (3-Fluoro-azetidin-1-yl)-[(2S,4S)-4-(4-oxazolo[5,4-b]pyridin-2-yl-piperazin-1-yl)-pyrrolidin-2-yl]-methanone | 375.4 |
| 93 | (3-Fluoro-azetidin-1-yl)-{(2S,4S)-4-[4-(3-trifluoromethyl-pyridin-2-yl)-piperazin-1-yl]-pyrrolidin-2-yl}-methanone | 402.4 |
| 94 | (3-Fluoro-azetidin-1-yl)-[(2S,4S)-4-(4-oxazolo[5,4-c]pyridin-2-yl-piperazin-1-yl)-pyrrolidin-2-yl]-methanone | 375.4 |
| 95 | [(2S,4S)-4-(2-Cyclopropyl-7,8-dihydro-5H-pyrido[4,3-d]pyrimidin-6-yl)-pyrrolidin-2-yl]-(3-fluoro-azetidin-1-yl)-methanone | 346.4 |
| 96 | 2-{4-[(3S,5S)-5-(3-Fluoro-azetidine-1-carbonyl)-pyrrolidin-3-yl]-piperazin-1-yl}-nicotinonitrile | 359.4 |
| 97 | (3-Fluoroazetidin-1-yl)((2S,4S)-4-(4-(5-(trifluoromethyl)pyridin-2-yl)piperazin-1-yl)pyrrolidin-2-yl)methanone | 402.4 |
| 98 | (3-Fluoro-azetidin-1-yl)-[(2S,4S)-4-(2-trifluoromethyl-7,8-dihydro-5H-pyrido[4,3-d]pyrimidin-6-yl)-pyrrolidin-2-yl]-methanone | 374.4 |
| 99 | (3-Fluoro-azetidin-1-yl)-{(2S,4S)-4-[4-(4-methyl-pyrimidin-2-yl)-piperazin-1-yl]-pyrrolidin-2-yl}-methanone | 349.4 |
| 100 | (3-Fluoro-azetidin-1-yl)-{(2S,4S)-4-[4-(2-trifluoromethyl-quinolin-4-yl)-piperazin-1-yl]-pyrrolidin-2-yl}-methanone | 452.5 |
| 101 | [(2S,4S)-4-(4-Benzooxazolo-2-ylpiperazin-1-yl)-pyrrolidin-2-yl]-((3R*,4S*)-3,4-difluoro-pyrrolidin-1-yl)-methanone | 406.4 |
| 102 | ((3R*,4S*)-3,4-Difluoro-pyrrolidin-1-yl)-[2S,4S)-4-(2-trifluoromethyl-7,8-dihydro-5H-pyrido[4,3-d]pyrimidin-6-yl)-pyrrolidin-2-yl]-methanone | 406.4 |
| 103 | ((3R*,4S*)-3,4-Difluoro-pyrrolidin-1-yl)-[(2S,4S)-4-(4-oxazolo[5,4-c]pyridin-2-yl-piperazin-1-yl)-pyrrolidin-2-yl]-methanone | 407.4 |
| 104 | ((3R*,4S*)-3,4-Difluoro-pyrrolidin-1-yl)-[(2S,4S)-4-(4-oxazolo[5,4-b]pyridin-2-yl-piperazin-1-yl)-pyrrolidin-2-yl]-methanone | 407.4 |
| 105 | ((3R*,4S*)-3,4-Difluoro-pyrrolidin-1-yl)-{(2S,4S)-4-[4-(4-methyl-pyrimidin-2-yl)-piperazin-1-yl]-pyrrolidin-2-yl}-methanone | 381.4 |
| 106 | (3,3-Difluoro-azetidin-1-yl)-{(2S,4S)-4-[4-(3-trifluoromethyl-pyridin-2-yl)-piperazin-1-yl]-pyrrolidin-2-yl}-methanone | 420.2 |
| 107 | 2-{4-[(3S,5S)-5-(3,3-Difluoro-azetidin-1-carbonyl)-pyrrolidin-3-yl]-piperazin-1-yl}-nicotinonitrile | 377.2 |
| 108 | (3,3-Difluoro-azetidin-1-yl)-[(2S,4S)-4-(2-trifluoromethyl-7,8-dihydro5H-pyrido[4,3-d]pyrimidin-6-yl)-pyrrolidin-2-yl]-methanone | 392.2 |
| 109 | (3,3-Difluoro-azetidin-1-yl)-{(2S,4S)-4-[4-(2-trifluoromethyl-quinolin-4-yl)-piperazin-1-yl]-pyrrolidin-2-yl}-methanone | 470.2 |
| 110 | (3,3-Difluoro-azetidin-1-yl)-[(2S,4S)-4-(4-oxazolo[5,4-c]pyridin-2-yl-piperazin-1-yl)-pyrrolidin-2-yl]-methanone | 393.2 |
| 111 | {(2S,4S)-4-[5-(4-Chloro-phenyl)-2-aza-bicyclo[2.2.1]hept-2-yl]-pyrrolidin-2-yl}-(3,3-difluoro-pyrrolidin-1-yl)-methanone | 410.2 |
| 112 | (3,3-Difluoro-pyrrolidin-1-yl)-[(2S,4S)-4-(2-trifluoromethyl-5,8-dihydro-6H-pyrido[3,4-d]pyrimidin-7-yl)-pyrrolidin-2-yl]-methanone | 406.1 |

EXAMPLE 113

(3,3-Difluoropyrrolidin-1-yl)-((2S,4S)-4-(4-(pyrimidin-2-yl)piperazin-1-yl)pyrrolidin-2-yl)-methanone

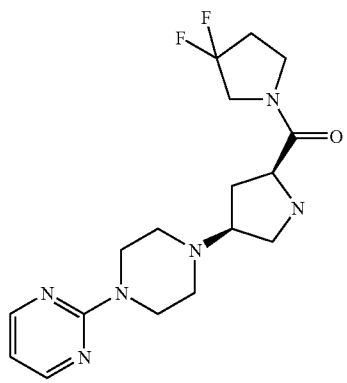

Step 1—(S)-2-(3,3-Difluoro-pyrrolidine-1-carbonyl)-4-oxo-pyrrolidine-1-carboxylic acid tert-butyl ester (S)-4-Oxo-pyrrolidine-1,2-dicarboxylic acid 1-tert-butyl ester (6.6 kg, 1.0 equivalent) was charged to a reactor, followed by addition of dichloromethane (15 volumes). The reaction mixture was cooled to 0° C. Triethylamine (4.82 liters, 1.2 equiv) was added over 30 minutes. The mixture turned from suspension to a clear solution at the end of triethylamine addition. The mixture was held at 0° C. to 5° C. for 10 minutes. Pivaloyl chloride (3.65 kg, 1.05 equivalents) was added slowly while keeping the reaction temperature at 0° C. to 5° C. The reaction mixture turned back to a slurry. The reaction mixture was sampled for completion by HPLC (using diethylamine to derivatize) after held for 1 hour at 0° C. to 5° C. 3,3-Difluoro-pyrrolidine hydrochloride (4.13 kg, 1.0 equivalent) was charged to the above mixture over 10 minutes at −10° C. to 0° C. Triethylamine (4.0 liters, 1.0 equiv) was introduced slowly over 70 minutes at −10° C. to 0° C. Upon completion of triethylamine addition, the mixture was stirred for 1 h at 0 to 5° C. The reaction was complete by HPLC assay (~1% starting material). The reaction was quenched with water (10 volumes) at 0° C. to 5° C. The mixture was heated to 20° C. to 25° C. The layers were separated, organic layer was washed with 0.5 M HCl (5 volumes). The organic layer was again washed with combined 5% NaHCO₃ (2 volumes) and half saturated brine solution (1.64 M, 3 volumes). The organic solution was concentrated atmospherically to a low stirrable volume (approximately 20 liters). Ethyl acetate (12.6 volumes, 82.8 liters) was added, the solution was concentrated atmospherically to ~6 volumes. The mixture was held at 60° C. to 65° C. for 2 hours and cooled to room temperature over 3 hours. The mixture was held at 20° C. to 25° C. for 8 hours. Heptane (8 volumes) was added, and the mixture was granulated for a minimum of 2 hours. The solid was filtered, rinsed with 2:1 heptane/ethyl acetate (1 volume), and dried in a tray dryer at 25° C. to 35° C. for a minimum of 12 h. Yield: 7.26 kg, 79%. HPLC purity: 99.7%. The mother liquor (86 liters) was concentrated to 12 liters under partial vacuum at 65° C. to 70° C. The mixture was cooled to 60° C. to 65° C. Ethyl acetate (4.0 liters) was added slowly over 15 minutes. The mixture was cooled to 20° C. to 25° C. over 2 hours and was held at that temperature for at least 2 hours. The solid was filtered and rinsed with heptane/ethyl acetate (3:1 v/v, 1.7 liters). Drying in a tray dryer for 12 hours at 35° C. to 45° C. yielded 435 grams of product. HPLC purity: 96.4%.

Step 2—(2S,4S)-2-(3,3-Difluoro-pyrrolidine-1-carbonyl)-4-(4-pyrimidin-2-yl-piperazin-1-yl)-pyrrolidine-1-carboxylic acid tert-butyl ester A reactor was charged with THF (20 volumes), 2-piperazin-1-yl-pyrimidine (2.17 kg, 1.05 equivalents) and the product from Step 1 (4.00 kg, 1.0 equivalent). The mixture was held at 20° C. to 25° C. until all material was dissolved over 30 minutes. Acetic acid (0.792 kg, 1.05 equivalents) as added. The mixture was stirred for 1 hour during which the reaction mixture turned to cloudy. The reaction mixture was refluxed for 30 minutes and then concentrated at 60° C. to 70° C. until a steady temperature of 66.9° C. was observed in the overheads indicating complete removal of water from the system. More THF was added as necessary. At the end, THF was added to bring the total volume in the reactor to 15 volumes of the limit reagent. The reaction mixture was cooled to −3° C. to 7° C. and sampled for complete formation of imine by HPLC (using sodium triacetoxyborohydride to reduce imine). Sodium triacetoxyborohydride (5.33 kg, 2.0 equivalents) was added portion-wise to the suspension at −5° C. to 15° C. The reaction mixture was heated to 20° C. to 25° C. and held for 12 hours. HPLC results confirmed the reaction was complete by 99.8%. Sodium bicarbonate aqueous solution (10% w/w, 10 volumes) was added. The slurry was concentrated to remove 10 volumes of THF under partial vacuum at 30° C. to 60° C. Ethyl acetate (10 volumes) was added to the suspension after it cooled to 20° C. to 25° C. The organic phase was separated and the aqueous phase was checked by HPLC. It contained less than 2% of the product. The organic phase was washed with water (5 volumes), saturated brine solution (5 volumes) and concentrated to a small volume (2 volumes) under partial vacuum at 45° C. to 50° C. To the slurry was added heptane (10 volumes) at 45° C. to 50° C. over 30 minutes. The mixture was cooled to 20° C. to 25° C. and granulated for 2 hours. Solid was collected by filtration, rinsed with heptane (2 volumes). Drying in a tray dryer for 12 hours at 35° C. to 45° C. yield 5.35 kg (91.3%) of the product.

Step 3—(3,3-Difluoro-pyrrolidin-1-yl)-[(2S,4S)-4-(4-pyrimidin-2-yl-piperazin-1-yl)-pyrrolidin-2-yl]-methanone Water (19 liters, 2 volumes) was charged to a reactor followed by the product from Step 2 (9.57 kg, 1.0 equivalent). To the slurry was added concentrated HCl (37 wt % in water, 19.1 liters, 2 volumes) slowly at 20° C. to 30° C. over 4 hours. The slurry went into solution after 12 liters of HCl was added. After the addition completion, the reaction was complete by HPLC assay. The reaction mixture was cooled to 5° C. to 15° C. To the mixture was added 50% NaOH aqueous solution slowly with agitation to pH 10 to pH 11. The pH was monitored with a pH meter closely during the neutralization. The total volume of 50% NaOH added was 12.45 liters. The mixture was warmed to 20° C. to 25° C. and extracted with ethyl acetate twice (115 liters, 12 volumes and 57 liters, 6 volumes, respectively). The sample from aqueous layer after second extraction was analyzed by HPLC and showed only 1% of the product in that aqueous solution. The organic layers were combined and treated with magnesium sulfate (5 kg) for 1 hour. The mixture was filtered. The filter cake was rinsed with ethyl acetate (10 liters). The filtrate was charged back to the reactor via a 0.2 micron in-line filter for speck free operation. (The following operations were performed under speck free conditions.) The solution was concentrated to 20 liters (2 volumes) under partial vacuum at 50° C. to 60° C. The mixture was cooled to 20° C. to 25° C. over 30 minutes. Upon cooling to room temperature, crystallization occurred. The mixture was held for 30 minutes. Hexanes (20 liters, 2 volumes) was added slowly over 1 hour. The mixture was granulated for 2 hours. The solid product was collected by filtration and rinsed with hexanes/ethyl acetate (10 liters, 1:1 v/v). The filter was blown dry with nitrogen for a minimum of 2 hours. The product was dried in a tray dryer at 44° C. for 12 hours. Yield: 5.7 kg, 75.9%. m.p. 156° C. MS m/z 367 (MH$^+$). $^1$H NMR (400 MHz, D$_2$O): δ 8.15 (d, 2H, J=5.0 Hz, CH of pyrimidine), 6.55 (t, 1H, J=4.8 Hz, CH of pyrimidine), 3.87-3.81 (dd, 1H, H$_{2b}$ of proline, rotomeric), 3.78-3.50 (m, 4H, N—CH$_2$ of pyrrolidide), 3.55-3.40 (m, 4H, N—CH$_2$ of piperazine), 2.97 (dd, 1H, J=10.2, 6.6 Hz, H$_{5a}$ of proline), 2.85-2.75 (m, 1H, H$_{4b}$ of proline), 2.69 (dd, 1H, J=10.0, 9.1 Hz, H$_{5b}$ of proline), 2.55-2.20 (m, 7H, overlapping N—CH$_2$ of piperazine, CH$_2$ of pyrrolidide and H$_{3b}$ of proline), 1.47-1.38 (m, 1H, H$_{3a}$ of proline).

Alternatively, the dihydrochloride salt of the titled compound was prepared according to the method of Example 1.

EXAMPLE 114

{(2S,4S)-[4-(4-pyrimidin-2-yl-piperazin-1-yl)-pyrrolidin-2-yl]}-(3,3,4,4-tetrafluoro-pyrrolidin-1-yl)-methanone dihydrochloride Step 1—tert-Butyl (2S,4S)-4-(4-pyrimidin-2-ylpiperazin-1-yl)-2-[(3,3,4,4-tetrafluoropyrrolidin-1-yl) carbonyl]pyrrolidine-1-carboxylate DIPEA (261 mL, 1.5 mmol) was added dropwise to a suspension of the title compound of Preparation 3 (114 mg, 0.3 mmol), HATU (128 mg, 0.33 mmol), and 3,3,4,4-tetrafluoropyrrolidine hydrochloride (54 mg, 0.3 mmol) in 5 mL dichloromethane. After stirring overnight, saturated sodium bicarbonate solution was added, the mixture was extracted with dichloromethane, the extracts dried over magnesium sulfate, and concentrated. The residue was purified by chromatography (Biotage® Flash 40S, EtOAc) to afford the title compound. MS m/z 503 (MH$^+$).

Step 2

An EtOAc/MeOH solution of the product from Step 1 was treated with 4M HCl in dioxane (ca. 5 mL). After 18 hr, the solvent was removed and the residue was taken up in acetonitrile and concentrated. The solid was taken up in hexanes, filtered, and dried to afford 50 mg (33%, two steps) of the title compound. MS m/z 403 (MH$^+$).

Using appropriate starting materials, the hydrochloride salts of the compounds of Examples 115 to 122, disclosed in Table 2, were prepared in a manner analogous to that described in Example 114.

TABLE 2

| Example | Name | MS (M + 1) |
|---|---|---|
| 115 | (3-Fluoroazetidin-1-yl)-((2S,4S)-4-(4-(pyrimidin-2-yl)piperazin-1-yl)pyrrolidin-2-yl)-methanone | 335 |
| 116 | ((3R*,4R*)-3,4-Difluoropyrrolidin-1-yl)-((2S,4S)-4-(4-(pyrimidin-2-yl)piperazin-1-yl)pyrrolidin-2-yl)-methanone | 367 |
| 117 | ((S)-3-Fluoropyrrolidin-1-yl)-((2S,4S)-4-(4-(pyrimidin-2-yl)piperazin-1-yl)pyrrolidin-2-yl)-methanone | 349 |
| 118 | ((R)-3-Fluoropyrrolidin-1-yl)-((2S,4S)-4-(4-(pyrimidin-2-yl)piperazin-1-yl)pyrrolidin-2-yl)-methanone | 349 |
| 119 | (3,3-Difluoroazetidin-1-yl)((4S)-4-(4-(pyrimidin-2-yl)piperazin-1-yl)pyrrolidin-2-yl)methanone | 353.3 |
| 120 | (2S,4S)-4-Fluoro-1-[(2S,4S)-4-(4-pyrimidin-2-yl-piperazin-1-yl)-pyrrolidine-2-carbonyl]-pyrrolidine-2-carbonitrile | 374.1 |
| 121 | (S)-4,4-Difluoro-1-[(2S,4S)-4-(2-trifluoromethyl-7,8-dihydro-5H-pyrido[4,3-d]pyrimidin-6-yl)-pyrrolidine-2-carbonyl]-pyrrolidine-2-carbonitrile | 431.2 |
| 122 | (2S,4S)-4-Fluoro-1-[(2S,4S)-4-(2-trifluoromethyl-7,8-dihydro-5H-pyrido[4,3-d]pyrimidin-6-yl)-pyrrolidine-2-carbonyl]-pyrrolidine-2-carbonitrile | 413.3 |
| 123 | (Azetidin-1-yl)((2S,4S)-4-(4-(pyrimidin-2-yl)piperazin-1-yl)pyrrolidin-2-yl)methanone | 317 |

EXAMPLE 124

((2S,3R,4S)-4-(4-(3-(Trifluoromethyl)pyridin-2-yl) piperazin-1-yl)-3-methylpyrrolidin-2-yl)(3,3-difluoropyrrolidin-1-yl)methanone dihydrochloride Step 1

The title compound of Preparation 1 (5.6 g, 20 mmol) was dissolved in benzene (50 mL) containing 4 Å molecular sieves (7.9 g) and treated with pyrrolidine (2.0 mL, 24 mmol). The solution was filtered and concentrated to dryness, leaving an orange foam (7.0 g, 100% yield).

Step 2

A solution of the product of Step 1 (7.0 g, 20 mmol) in acetonitrile (100 mL) was added to crushed potassium carbonate (5.2 g, 38 mmol) and treated with methyl iodide (1.5 mL, 24 mmol). The mixture was heated to 90° C. for 16 hrs, cooled to RT, and concentrated. The residue was taken up in chloroform (150 mL) and a mixture of AcOH (5 mL) and water (45 mL) was added. After three hr at RT, the layers were separated, the aqueous layer was extracted with chloroform (3×25 mL), and the combined organic phases were washed with saturated sodium bicarbonate (2×25 mL) and brine, and concentrated to a brown oil. The oil was dissolved in ether (75 mL), filtered, and concentrated to a pale brown solid (0.97 g, 16% yield).

Step 3

To a mixture of the product of Step 2 (74 mg, 0.25 mmol), 1-(3-trifluoromethyl)pyridin-2-yl-piperazine (63 mg, 0.28 mmol), AcOH (16 µL), and sodium acetate (23 mg, 0.28 mmol) in MeOH (1 mL) was added sodium cyanoborohydride (21 mg, 0.28 mmol). The mixture was stirred at RT for 65 hr and then concentrated. The residue was taken up in EtOAc (20 mL) and the solution was washed with 1N sodium hydroxide (2×3 mL) and brine (5 mL), dried over magnesium sulfate, and concentrated to dryness. The residue was purified by preparative HPLC (Shimadzu, Columbia, Md.; 30×50 cm Waters-Xterra® C18 column—Waters Instrument Co., Milford, Mass.; 30 mL/min gradient of 15% acetonitrile with 0.1% ammonium hydroxide over 10 min) to afford a colorless solid (35.7 mg, 26% yield).

Step 4

HCl (4M) in dioxane (0.5 mL) was added to a solution of the product of Step 3 (35 mg, 0.064 mmol) in acetonitrile (1 mL). After 16 hr, the mixture was concentrated to dryness and the residue was triturated with ether (2 mL). The title compound was obtained as a solid (32 mg, 96% yield). MS m/z 448.4 (MH$^+$).

Using appropriate starting materials, the hydrochloride salts of the compounds of Examples 125 to 127, disclosed in Table 3 hereinbelow, were prepared in a manner analogous to that described in Example 124.

TABLE 3

| Example | Name | MS (M + 1) |
|---|---|---|
| 125 | ((2S,3R,4S)-4-(4-(2-tert-Butyl-5-(trifluoromethyl)pyrazolo[1,5-a]pyrimidin-7-yl)piperazin-1-yl)-3-methylpyrrolidin-2-yl)(3,3-difluoropyrrolidin-1-yl)methanone | 544.5 |
| 126 | (3,3-Difluoro-pyrrolidin-1-yl)-{(2S,3R,4S)-3-methyl-4-[4-(5-trifluoromethyl-pyridin-2-yl)-piperazin-1-yl]-pyrrolidin-2-yl}-methanone | 448.4 |
| 127 | (3,3-Difluoro-pyrrolidin-1-yl)-[(2S,3R,4S)-3-methyl-4-(4-pyrimidin-2-yl-piperazin-1-yl)-pyrrolidin-2-yl]-methanone | 381.4 |

EXAMPLE 128

(2,4-Difluoro-phenyl)-{4-[(3S,5S)-5-(3,3-difluoro-pyrrolidine-1-carbonyl)-pyrrolidin-3-yl]-piperazin-1-yl}-methanone dihydrochloride Step 1—(2S,4S)-4-[4-(2,4-Difluoro-benzoyl)-piperazin-1-yl]-2-(3,3-difluoro-pyrrolidine-1-carbonyl)-pyrrolidine-1-carboxylic acid tert-butyl ester The title compound of Preparation 7 (97 mg, 0.25 mmol), 2,4-difluorobenzoic acid (40 mg, 0.25 mmol) and HATU (95 mg, 0.3 mmol) were mixed in anhydrous methylene chloride under nitrogen and cooled to 0° C. in and ice bath before addition of DIEA (32 mg, 45 µL, 0.3 mmol). The reaction mixture was allowed to warm to RT and stirred overnight. The reaction was quenched with saturated sodium bicarbonate and the aqueous layer was extracted with methylene chloride The combined organic extracts were washed with brine and dried over magnesium sulfate. The crude product was purified by flash chromatography using methylene chloride:MeOH (95:5) to give the final product as white powder (132 mg, 100%). MS m/z 529.4 (MH$^+$).

Step 2—An acetonitrile solution of the product of Step 1 (120 mg) was treated with 4N HCl in dioxane (1 mL). The reaction was stirred at RT overnight and evaporated. The residue was dissolved in water, filtered, lyophilized overnight to afford the title product as white powder (110 mg, 96%). MS m/z 429.2 (MH+).

Using appropriate starting materials, the hydrochloride salts of the compounds of Examples 129 to 133, disclosed in Table 4, were prepared in a manner analogous to that described in Example 128.

TABLE 4

| Example | Name | MS (M + 1) |
|---|---|---|
| 129 | (3,3-Difluoro-pyrrolidin-1-yl)-{(2S,4S)-4-[4-(toluene-4-sulfonyl)-piperazin-1-yl]-pyrrolidin-2-yl}-methanone | 443.2 |
| 130 | (3-Amino-pyrazin-2-yl)-{4-[(3S,5S)-5-(3,3-difluoro-pyrrolidin-1-carbonyl)-pyrrolidin-3-yl]-piperazin-1-yl}-methanone | 410.2 |
| 131 | {4-[(3S,5S)-5-(3,3-Difluoro-pyrrolidine-1-carbonyl)-pyrrolidin-3-yl]-piperazin-1-yl}-quinolin-4-yl-methanone | 444.3 |
| 132 | 4-[(3S,5S)-5-(3,3-Difluoro-pyrrolidine-1-carbonyl)-pyrrolidin-3-yl]-piperazine-1-carboxylic acid-ethylamide | 360.2 |
| 133 | 4-[(3S,5S)-5-(3,3-Difluoro-pyrrolidine-1-carbonyl)-pyrrolidin-3-yl]-piperazine-1-carboxylic acid-(4-fluoro-phenyl)-amide | 426.2 |

Biological Methodologies

The utility of the compounds of formula (I), the prodrugs and stereoisomers thereof, and the pharmaceutically acceptable salts of the compounds, prodrugs, and stereoisomers, in the treatment or prevention of the conditions enumerated hereinabove in mammals may be demonstrated in conventional assays known to one of ordinary skill in the relevant art, including the in vivo and in vitro assays described below. Such assays also provide a means by which the activities of the compounds of formula (I), the prodrugs, and stereoisomers thereof, and the pharmaceutically acceptable salts of the compounds, prodrugs, and stereoisomers, may be compared with the activities of other compounds.

In vitro Assay for DPP-IV Inhibition

DPP-IV inhibition may be demonstrated in vitro by the following assay, which is adapted from methods of Scharpe, et al., A. Clin. Chem., 2299 (1988) and Lodja, Z. Czechoslovak Medicine, 181 (1988). 150 µL of an enzyme-substrate solution is pipetted into microtiter wells of a polystyrene 96-well plate, and maintained at 4° C. The enzyme-substrate solution comprises 50 µM Gly-Pro-4-methoxy-β-naphthylamide hydrochloride in 50 mM Tris assay buffer pH 7.3 containing 0.1M sodium chloride, 0.1% (v/v) Triton and 50 µU/mL DPP-IV (MP Biomedicals, Livermore, Calif.; DPP-IV 5 mU/mL stock). 5 µL per well of the compound of formula (I) is added, bringing the final concentrations of the formula (I) compound to between 3 µM and 10 nM per well.

Controls. Enzyme is omitted from four (4) wells, as a reagent blank. 5 μL of 3 mM Diprotin A (Bachem Bioscience, Inc.; King of Prussia, Pa.) is added to four wells as a positive quality control, providing a final Diprotin A concentration of 100 μM. To measure total enzyme activity (i.e., a negative control), without the influence of any compounds of formula (I), 5 μL of distilled water is added to four wells.

The entire assay is incubated overnight (between 14 and 18 hours) at 37° C. The reaction is quenched by adding 10 μL of Fast Blue B solution (0.5 mg/mL Fast Blue B in a buffer comprising 0.1M sodium acetate pH 4.2 and 10% (v/v) Triton X-100 to each well, followed by shaking for approximately 5 min at room temperature. The plates may be analyzed on a Spectramax spectrophotometer (Molecular Devices; Sunnyvale, Calif.), or equivalent equipment, (absorption maximum at 525 nm). $IC_{50}$ data for compounds may be obtained by measuring the activity of DPP-IV over a range of compound concentrations from 10 nM to 3 μM.

In Vivo Assay for Glucose Lowering

The glucose lowering effects of DPP-IV inhibitors, including the compounds of formula (I), may be exemplified in 4-6 week old KK/H1J mice (Jackson Labs; Bar Harbor, Me.) in the context of an oral glucose tolerance test.

Oral glucose tolerance tests (OGTT) have been in use in humans since, at least, the 1930s, as described by Pincus, et al., Am. J. Med. Sci., 782 (1934), and are routinely used in the diagnosis of human diabetes, though not to evaluate the efficacy of therapeutic agents in patients.

KK mice have been used to evaluate (i) glitazones (Fujita et al. Diabetes, 804 (1983); Fujiwara, et al., Diabetes, 1549 (1988); and Izumi, et al., Biopharm Drug. Dispos., 247 (1997)); (ii) metformin (Reddi, et al., Diabet. Metabol., 44 (1993)); (iii) glucosidase inhibitors (Hamada, et al., Jap. Pharmacol. Ther., 17 (1988) and Matsuo et al., Am. J. Clin. Nutr., 314S (1992)), and (iv) extra-pancreatic effects of sulfonylureas (Kameda, et al., Arzneim. Forsch./Drug Res., 39044 (1982) and Muller et al., Horm. Metabl. Res., 469 (1990)).

KK mice are derived from an inbred line first established and described by Kondo, et al., Bull. Exp. Anim., 107 (1957). These mice spontaneously develop a hereditary form of polygenic diabetes that progresses to cause renal, retinal, and neurological complications analogous to those seen in human diabetic subjects, however, they do not require insulin or other medication for survival.

Another aspect of the invention is directed to the use of KK mice to evaluate the effects of insulin secretagogue agents in the context of an oral glucose tolerance test. The mice are fasted overnight (about 14 to about 18 hr), but allowed free access to water. After fasting, (time "t"=0), 25 μL of blood is drawn from the retro-orbital sinus and added to 0.025% heparinized saline (100 μL) on ice. The mice (10 per group) are then orally dosed with a solution of a compound of formula (I) in 0.5% methylcellulose (0.2 mL/mouse). Two controls groups receive only 0.5% methylcellulose. At t=15 min, the mice are bled, as described above, and then dosed with 1 mg/kg glucose in distilled water (0.2 mL/mouse). The first control group is dosed with glucose. The second control group is dosed with water. At t=45 min, the mice are again bled, as described above. The blood samples are centrifuged, the plasma collected and analyzed for glucose content on a Roche-Hitachi 912 glucose analyzer (Roche Diagnostics Corp.; Indianapolis, Ind.). The data may be expressed as percent (%) inhibition of glucose excursion relative to the two control groups (i.e., the glucose level in the animals receiving glucose but no test compound representing 0% inhibition and the glucose concentration in the animals receiving only water representing 100% inhibition).

The compounds of formula (I) generally exhibit inhibitory activity, expressed as $IC_{50}$'s, against DPP-IV that are <1,000 nM. Generally preferred compounds have $IC_{50}$'s <100 nM. For example, ((2S,4S)-4-(4-(3-cyanopyrazin-2-yl)piperazin-1-yl)pyrrolidin-2-yl)-((3R*,4S*)-3,4-difluoropyrrolidin-1-yl)-methanone dihydrochloride has an $IC_{50}$ of 3.5 nM.

Comparative Rat Pharmacokinetics Experiments

Rat Pharmacokinetics experiments were performed to demonstrate the improvement in plasma concentrations maintained over time for a compound of the present invention as compared to a structurally similar prior art compound generically disclosed in International Application WO 02/14271. Specifically, plasma concentrations over time were measured for rats administered (a) the dihydrochloride salt of (3,3-difluoropyrrolidin-1-yl)-((2S,4S)-4-(4-(pyrimidin-2-yl)piperazin-1-yl)pyrrolidin-2-yl)-methanone (hereinafter "CPD 113"), which was prepared as described in Example 113, and (b) the comparative dihydrochloride salt of ((2S,4S)-4-(4-(pyrimidin-2-yl)piperazin-1-yl)pyrrolidin-2-yl)(pyrrolidin-1-yl)methanone (hereinafter "comparator"), which may be prepared according to the method of Example 1 or as generally described in WO 02/14271.

In this experiment, male Sprague-Dawley rats (200-250 grams) implanted with jugular vein cannulas (JVC) were obtained from Charles River Laboratories. Each compound was administered to two rats or by oral gavage. The oral dose was administered as a solution in 0.5% methylcellulose with a dose volume of 10 mL/kg. The amount of each compound administered was 5 mg/kg body weight. Blood samples (0.25 mL) were collected at multiple time points from 0-24 hours and placed into tubes containing lithium heparin (Becton Dickinson, Microtainer®). The blood samples were then centrifuged at 12000 rpm for 10 minutes). Plasma aliquots were taken for determination of compound plasma concentrations (pharmacokinetic analysis). The plasma samples were frozen at −70° C. until analysis.

The rat plasma samples were analyzed for compound concentrations by LC/MS/MS (Applied Biosystems API 4000 mass spectrometer). In brief, compound standard curves were prepared in control rat plasma with a dynamic range of 1.0-2000 ng/mL. Aliquots (0.02 mL) of both standards and samples Were placed into Marsh™ tubes in a 96-well block. Proteins were precipitated by addition of 0.1 mL acetonitrile containing 0.1 μg/mL of internal standard. The 96-well blocks were vortexed and then centrifuged at 3000 rpm for 5 minutes. The resulting supernatant was removed and placed into a new 96-well block and taken to dryness at 50° C. under a nitrogen stream. Residues were reconstituted in mobile phase (60% 5 mM ammonium acetate and 40% acetonitrile). Aliquots (0.01 mL) were then injected onto the LC/MS/MS for analysis.

The average plasma concentrations, measured are provided in the following table.

| Compound/ Time (hr) | CPD 113 Mean Plasma Level ng/ml | Std dev | Comparator Mean Plasma Level ng/ml | Std dev |
|---|---|---|---|---|
| 0.25 | 1406.0 | 338.0 | 446 | 71.1 |
| 0.5 | 1322.5 | 359.9 | 425 | 108 |
| 0.75 | 979.2 | 137.0 | 319 | 59.8 |

-continued

| Compound/ Time (hr) | CPD 113 Mean Plasma Level ng/ml | Std dev | Comparator Mean Plasma Level ng/ml | Std dev |
|---|---|---|---|---|
| 1 | 768.2 | 314.0 | 283 | 13.3 |
| 2 | 289.2 | 71.8 | 128 | 40.4 |
| 4 | 97.8 | 69.2 | 27.3 | 11.2 |
| 6 | 49.3 | 19.1 | 12.7 | 1.2 |
| 8 | 32.8 | 25.5 | 6.16 | 2.62 |

As shown by their despective plasma concentrations, CPD 113 achieved and maintained significantly higher plasma concentrations than did the comparator compound.

We claim:

1. (3,3-Difluoropyrrolidin-1-yl)-((2S,4S)-4-(4-(pyrimidin-2-yl) piperazin-1-yl)pyrrolidin-2-yl)methanone, or a pharmaceutically acceptable salt thereof, or a solvate of said salt.

2. A pharmaceutical composition comprising:
   (a) (3,3-difluoropyrrolidin-1-yl)-((2S,4S)-4-(4-(pyrimidin-2-yl) piperazin-1-yl)pyrrolidin-2-yl)methanone, or a pharmaceutically acceptable salt of said compound, or a solvate of said salt; and
   (b) a pharmaceutically acceptable carrier, vehicle, diluent or excipient.

3. A method of treating a condition, selected from the group consisting of Type 2 diabetes, Type 1 diabetes, hyperglycemia, metabolic syndrome, impaired glucose tolerance, diabetic neuropathy, diabetic nephropathy, diabetic retinopathy and diabetic cardiomyopathy, comprising administering to a mammal, in need of such treatment, a therapeutically effective amount of (3,3-difluoropyrrolidin-1-yl)-((2S,4S)-4-(4-(pyrimidin-2-yl) piperazin-1-yl)pyrrolidin-2-yl)methanone or a pharmaceutically acceptable salt of said compound, or a solvate of said salt.

4. The method of claim 3 wherein said mammal is a human.

* * * * *